United States Patent [19]

Skuballa et al.

[11] 4,004,020
[45] Jan. 18, 1977

[54] NOVEL PROSTANOIC ACID DERIVATIVES AND PROCESS FOR THE PREPARATION THEREOF

[75] Inventors: Werner Skuballa; Bernd Raduchel; Helmut Vorbruggen; Walter Elger; Wolfgang Losert; Olaf Loge, all of Berlin, Germany

[73] Assignee: Schering Aktiengesellschaft, Berlin & Bergkamen, Germany

[22] Filed: Dec. 19, 1974

[21] Appl. No.: 534,483

[30] Foreign Application Priority Data

Dec. 21, 1973 Germany .................. 2365101

[52] U.S. Cl. .................. 424/278; 260/240 R; 260/340.3; 260/340.5; 260/340.7; 260/340.9; 260/514 D; 260/468 R; 260/468 D; 260/611 R; 424/282; 424/305; 424/317; 424/318; 424/312; 424/339
[51] Int. Cl.² .................. A01N 9/28; A61K 31/335
[58] Field of Search ......... 260/240 R, 340.6, 340.7, 260/340.9, 340.5, 468 D; 424/278, 282

[56] References Cited
UNITED STATES PATENTS

| 3,833,612 | 9/1974 | Wendler et al. | 260/340.9 |
| 3,845,042 | 10/1974 | Strike et al. | 260/240 R |
| 3,850,952 | 11/1974 | Kuo et al. | 260/340.9 |
| 3,864,387 | 2/1975 | Nelson | 260/514 D |
| 3,873,570 | 3/1975 | Kelly | 260/340.9 |

Primary Examiner—Arthur P. Demers
Attorney, Agent, or Firm—Millen, Raptes & White

[57] ABSTRACT

Prostaglandins of the formula

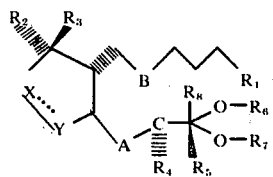

wherein $R_1$ is hydroxymethyl, carboxy, aryloxycarbonyl, alkoxycarbonyl of 1-8 carbon atoms in the alkoxy group, or the group $-COO-CH_2-U-V$ wherein U is a direct C-C bond, carbonyl or carbonyloxy and V is phenyl substituted by phenyl, alkoxy of 1-2 carbon atoms or halogen; $R_2$ is hydroxy and $R_3$ is a hydrogen atom or $R_2$ and $R_3$ collectively are an oxygen atom; A is $-CH_2-CH_2-$ or trans-$CH=CH$; B is $-CH_2-CH_2-$ or $CH=CH$; one of $R_4$ and $R_5$ is hydroxy and the other is a hydrogen atom; $R_6$ and $R_7$ each are alkyl of 1–10 carbon atoms or collectively are alkylene of up to 7 carbon atoms and with 2-3 carbon atoms in the chain, phenylene or naphthylene; $R_8$ is a hydrogen atom or alkyl of 1-5 carbon atoms;

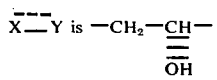

when $R_2$ is hydroxy and $R_3$ is a hydrogen atom or is

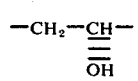

or $-CH=CH-$ when $R_2$ and $R_3$ collectively are an oxygen atom; or, when $R_1$ is carboxy, a physiologically acceptable salt thereof with a base, possess the activity of the corresponding natural prostaglandins, including a luteolytic effect, and are useful in triggering abortions and syncronizing the conception cycle of mammals.

29 Claims, No Drawings

NOVEL PROSTANOIC ACID DERIVATIVES AND PROCESS FOR THE PREPARATION THEREOF

BACKGROUND OF THE INVENTION

This invention relates to novel prostanoic acid derivatives, processes for the production thereof, as well as novel intermediates formed during this process.

The novel prostanoic acid derivatives exhibit a pharmacological spectrum of activity similar to that of the natural prostaglandins and are useful for similar purposes.

Prostaglandins are $C_{20}$-unsaturated fatty acids showing a great variety of physiological effects (T. O. Oesterling et al., J. Pharmaceutical Sciences 61 [(1972] 1861-1895). Such effects are, for example, vasodilation, bronchodilatation, inhibition of gastric acid secretion, inhibition of blood platelet aggregation. Various natural prostaglandins, such as, for example prostaglandin $E_2$ and prostaglandin $F_{2\alpha}$, are suitable for bringing about the onset of menstruation, for the induction of abortion, and for the induction of labor.

The conventional prostaglandins are derivatives of prostanoic acid having the following formula:

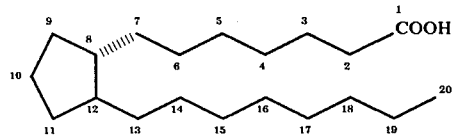

Examples of known prostaglandins, called PG hereinbelow, are:

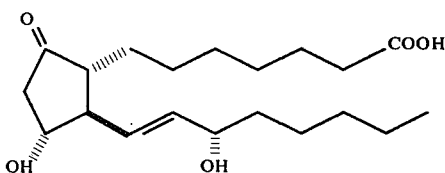

PG $E_1$

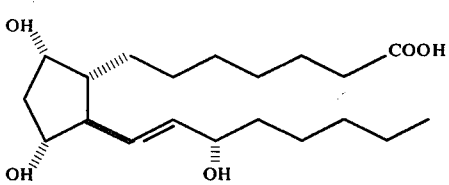

PG $f_1$

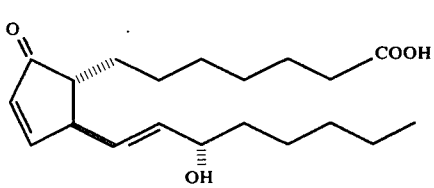

PG $A_1$

PG $E_2$, PG $F_{2\alpha}$, PG $A_2$ correspond to the compounds of the PG′$_1$ series with respect to their basic structure, except the linking of the number 5 and 6 carbon atoms is different. In the PG′$_2$ series, the C-5 and C-6 carbon atoms are linked by a cis-double bond.

PG $F_{2\alpha}$ has the following formula:

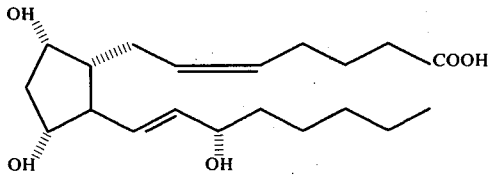

PG $E_3$, PG $F_{3\alpha}$, and PG $A_3$ differ from the corresponding PG′$_2$ compounds in that the C-17 and C-18 carbon atoms are linked by a cis-double bond.

PG $F_{3\alpha}$ has the formula:

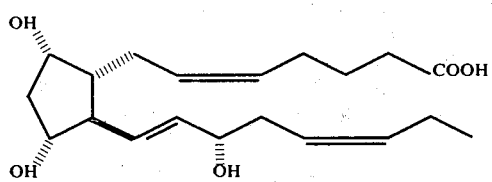

It is generally known that the physiological activities of the prostaglandins in the mammal organism as well as in vitro are only of a brief duration, since these substances are rapidly converted into pharmacologically inactive metabolic products. Thus, a physiologically inactive metabolite is formed by oxidation of the allyl hydroxy function on the C-15 carbon atoms by the action of 15-hydroxyprostaglandin dehydrogenases. For example, from PG $F_{2\alpha}$ the ensuing 13,14-dihydro-15-dehydro derivative is formed by this oxidation as well as by a hydrogenating step, as the main metabolite (E. Granström and B. Samuelson, Eur.J.Biochem. 10 [1969], 411):

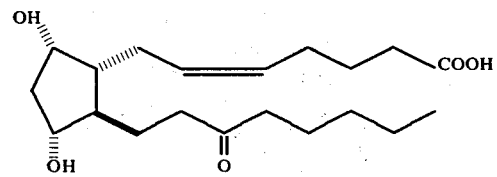

which possesses the physiological activities typical for this class of substances only to a very weakened extent.

Therefore, it is desirable to provide prostaglandin analogs having a spectrum of effectiveness comparable to that of the natural prostaglandins, and to make structural changes whereby the duration and selectivity of effectiveness are increased.

It has now been found that 16-dioxy derivatives of the prostaglandins exhibit surprisingly good physiological activities. These novel prostaglandin analogs satisfy the above-mentioned requirement, i.e., they are superior in their effectiveness to the natural prostaglandins. Moreover, the effect lasts over a longer period of time.

SUMMARY OF THE INVENTION

In a composition aspect, this invention relates to prostaglandins of the general Formula I

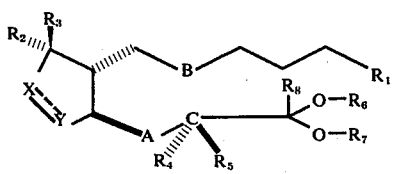

wherein $R_1$ is a hydroxymethyl, carboxyl, aryloxycarbonyl, alkoxycarbonyl of 1–8 carbon atoms in the alkoxy group or $-COO-CH_2-U-V$ wherein U is a direct bond, carbonyl or carbonyloxy and V is phenyl substituted by phenyl, alkoxy of 1–2 carbon atoms, or halogen atoms, preferably bromine atoms; $R_2$ is a hydroxyl group and $R_3$ is a hydrogen atom or $R_2$ and $R_3$ collectively are an oxygen atom; A is $-CH_2-CH_2$ or trans-$CH=CH$; B is $-CH_2-CH_2$ or cis-$CH=CH$; $R_4$ is hydroxy and $R_5$ is a hydrogen atom or $R_4$ is a hydrogen atom and $R_5$ is a hydroxyl group; $R_6$ and $R_7$ each are alkyl of 1-10 carbon atoms or collectively are a ring-forming bridging alkylene or arylene group, including alkylene of up to 7, preferably up to 5, carbon atoms and with 2–3 carbon atoms in the chain, e.g., unsubstituted arylene, e.g., phenylene, 2,3-naphthylene and 1,8-naphthylene; $R_8$ is a hydrogen atom or lower alkyl of 1-5 carbon atoms;

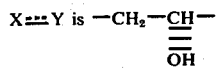

when $R_2$ is hydroxyl and $R_3$ is a hydrogen atom or either

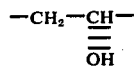

or $-CH=CH$ when $R_2$ and $R_3$ collectively are an oxygen atom; and when $R_1$ is carboxyl, physiologically acceptable salts thereof with bases.

In another composition aspect, this invention relates to pharmaceutical compositions comprising one or more compounds of Formula I or, when $R_1$ is carboxy, a physiologically acceptable salt thereof with a base.

DETAILED DISCUSSION

Examples of classes of compounds of Formula I are those wherein:
a. $R_1$ is carboxy;
b. $R_1$ is alkoxy carbonyl of 1–8 carbon atoms in the group, e.g., methyl, ethyl, propyl, isopropyl, butyl;
c. $R_1$ is $-COO-CH_2-U-V$, especially those wherein U is carbonyl and V is biphenyl;
d. $R_6$ and $R_7$ collectively are phenylene, especially those of (a), (b) and (c);
e. $R_6$ and $R_7$ collectively are naphthylene, preferably 2,3-naphthylene, especially those of (a), (b) and (c);
f. $R_6$ and $R_7$ collectively are alkylene of up to 7, preferably up to 5, carbon atoms and with 2–3 carbon atoms in the chain , e.g.,

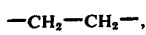

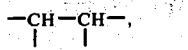

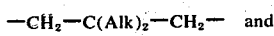

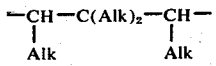

wherein Alk is alkyl of 1–2 carbon atoms, preferably methyl, especially those of (a), (b) and (c);
g. $R_2$ and $R_3$ collectively are an oxygen atom, especially those of each of (a) – (f);
h. $R_2$ is hydroxy and $R_3$ is a hydrogen atom; especially those of each of (a) – (f);
i. $R_8$ is a hydrogen atom, especially each of (a) – (h), above.

Examples of bases suitable for forming physiologically acceptable salts when $R_1$ is carboxy are: alkali hydroxides, e.g., sodium and potassium hydroxide, alkaline earth hydroxides, e.g., calcium hydroxide, ammonia, amines, e.g., ethanolamine, diethanolamine and other monoalkanol- and dialkanolamines, triethylamine and other trialkylamines, N-methylglucamine, morpholine and other heterocyclic amines, e.g., of 5–6 ring members, tris-(hydroxymethyl)methylamine, etc., alkyl and alkanol each preferably being of 1–4 carbon atoms.

Preferred when $R_6$ and $R_7$ are lower alkyl groups of 1–10 carbon atoms are ethyl, propyl, isopropyl, butyl, isobutyl and pentyl groups. Examples of substituents of phenylene or naphthylene $R_6$ and $R_7$ are one, two or more of halogen atoms, e.g., chlorine, bromine and fluorine atoms, alkyl and alkoxy, for example, methyl, ethyl, methoxy and ethoxy, and alkylidenedioxy. A particularly suitable alkylidenedioxy substituent is methylenedioxy. Other possible substituents are dialkylamino wherein the alkyls are preferably the same, for example dimethylamino.

When $R_8$ is lower alkyl, preferred are methyl and ethyl. In addition to the compounds of the examples, the following are illustrative compounds of this invention: (5Z,13E)-(8R,11R,12R,15R)-11,15-Dihydroxy-9-oxo-16,16-diathoxy-17,18,19,20-tetranor-prostadienoic acid, (5Z,13E)-(8R,9S,11R,12R,15R)-1,9,11,15-Tetrahydroxy-15-(1,3-dioxa-2-indanyl)-16,17,18,19,20-pentanor-prostadienoic acid and (5Z,13E)-(8R,9S, 11R,12R,15R)-9,11,15-Trihydroxy-15(2-methyl-1,3-dioxa-2-indanyl)-16,17,18,19,20-pentanor-prostadienoic acid.

The invention relates furthermore to a process for the preparation of the novel prostaglandins of general Formula I, characterized in that
a. compounds of general formula II below are hydrolyzed

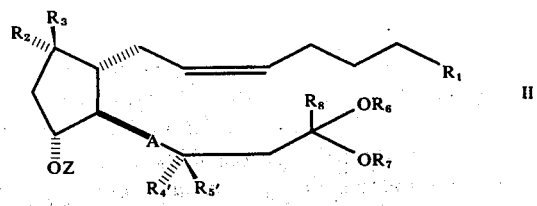

wherein

A, $R_1$, $R_2$, $R_3$, $R_6$, $R_7$, and $R_8$ have the values given for Formula I, $R_4'$ represents the group Z and
$R_5'$ represents a hydrogen atom, or
$R_4'$ represents a hydrogen atom and
$R_5'$ represents the group Z, and Z is a hydroxyl masking group which can readily be split off in an acidic medium, such as the tetrahydropyranyl or α-ethoxyethyl group; or b. lactones of general Formula III

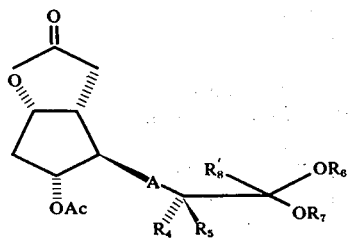

wherein

A, $R_4$, $R_5$, $R_6$, $R_7$, and $R_8$ have the values given for Formula I and Ac represents an aliphatic or aromatic acyl group, are treated with diisobutylaluminum hydride or lithium tritert.-butoxyaluminum hydride according to a simplified Corey synthesis as described in U.S. application Ser. No. 472,737 and the thus obtained lactols of general Formula IV

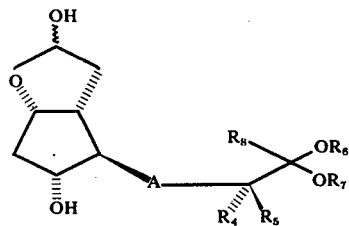

with A, $R_4$, $R_5$, $R_6$, $R_7$, and $R_8$ having the values given for Formula I,
are reacted with a Wittig reagent of general formula V

$Ph_3P=CH-(CH_2)_3R_1$   V wherein

Ph represents a phenyl group and
$R_1$ has the values given for Formula I but is preferably the carboxyl group; and depending on the lastly desired values for $R_1$, $R_2$, $R_3$, A, B, and X—Y in the final product of general Formula I, optionally in the compounds obtained according to (a) or (b) a 1-carboxy group is esterified and/or the 9-OH group is oxidized after intermediarily masking the 11- and 15-hydroxy groups by silylation (Chem. Comm. [1972]), 1120), and optionally the thus-obtained product is subsequently dehydrated with elimination of the 11-hydroxy group and/or the 13,14- and/or 5,6-double bond is hydrogenated and optionally the 1-carboxy compounds are converted into the salts thereof with physiologically compatible bases.

The hydrolysis according to process (a) is conducted according to conventional methods in an aqueous solution of an organic acid, such as, for example, acetic acid, propionic acid, etc., or in aqueous solution of an inorganic acid, e.g. hydrochloric acid. To improve the solubility, a watermiscible inert organic solvent is advantageously added. Suitable organic solvents are, for example, alcohols, such as methanol and ethanol, and ethers, such as dimethoxyethane, dioxane, and tetrahydrofuran. Tetrahydrofuran is preferably employed. The hydrolysis is preferably effected at temperatures of between 20° C. and 80° C. In case of compounds of the prostaglandin E-type, the hydrolysis is effected below 45° C. to avoid the formation of prostaglandin A-compounds as by-products.

According to process (b), a lactone of Formula III is reacted with an excess of diisobutylaluminum hydride or lithium tri-tert.-butoxyaluminum hydride at temperatures of between −100° C. and 0° C., preferably at −80° C. to −40° C., in an aprotic solvent, such as toluene, diethyl ether, tetrahydrofuran, or glyme. During this reaction, it is not only the lactone group which is reduced, but the ester group is also quantitatively split with the formation of a lactol of general Formula IV. The lactol of general Formula IV is then reacted with the Wittig reagent of general Formula V. The Wittig reagent can also be produced during the reaction from 4-$R_1$-butyltriphenylphosphonium bromide in an aprotic solvent, such as dimethyl sulfoxide of dimethylformamide, with an anhydrous base. Suitable anhydrous bases are especially sodium hydride, potassium tert.-butylate, and butyllithium. The reaction is accomplished at temperatures of between about 0° C. and 100° C., preferably at 30°–80° C.

The compounds obtained according to processes (a) and (b), respectively, can optionally be conventionally esterified, oxidized, dehydrated and/or hydrogenated thereafter. The free acids ($R_1$ = COOH) can be converted into the salts with physiologically acceptable bases.

To produce the esters of general Formula I wherein $R_1$ is an alkoxycarbonyl group of 1–8 carbon atoms in the alkoxy residue, the 1-carboxy compounds are reacted in a manner known per se with diazo hydrocarbons. The esterification with diazo hydrocarbons takes place, for example, by mixing a solution of the diazo hydrocarbon in an inert solvent, preferably in diethyl ether, with the 1-carboxy compound in the same or in another inert solvent, such as, for example, methylene chloride. After the reaction is finished, taking 1–30 minutes, the solvent is removed and the ester purified in the usual way.

Diazoalkanes are either known or can be prepared according to conventional methods (Org. Reactions, Vol. 8, pp. 389–394 [1954]).

To introduce the ester group -$CH_2$U-V- for $R_1$, the 1-carboxy compound of general Formula I is reacted, in the presence of an agent splitting off hydrogen halide, with a halogen compound of the general formula

Hal-$CH_2$-U-V wherein

Hal represents a halogen atom, preferably bromine,
U is a direct bond, a carbonyl group, or a carbonyloxy group, and
V is a phenyl ring substituted by phenyl groups, alkoxy groups of 1–2 carbon atoms, or halogen atoms, preferably bromine atoms.

Examples of suitable agents splitting off hydrogen halide are silver oxide, sodium carbonate, potassium carbonate, sodium bicarbonate, potassium bicarbonate, or amines, such as trimethylamine, triethylamine, tributylamine, trioctylamine, and pyridine. The reaction with the halogen compound is conducted in an inert solvent, preferably in acetone, acetonitrile, dimethylacetamide, dimethylformamide, or dimethyl sulfoxide at temperatures of −80° C. to +100° C., preferably at room temperature.

To produce the esters of general Formula I wherein $R_1$ is substituted or unsubstituted aryloxycarbonyl group, the 1-carboxy compound is reacted with the corresponding arylhydroxy compound in the usual manner, for example with dicyclohexylcarbodimmide in the presence of a suitable base, e.g. pyridine or triethylamine, in an inert solvent. Suitable solvents are methylene chloride, ethylene chloride, chloroform, ethyl acetate, tetrahydrofuran, but preferably chloroform. The reaction is accomplished at temperatures of between −30° C. and +50° C., preferably at +10° C.

Examples of suitable substituted or unsubstituted aryloxycarbonyl groups $R_1$ are: phenoxycarbonyl, 1-naphthyloxycarbonyl, and 2-naphthyloxycarbonyl, each of which can be substituted by 1–3 halogen atoms, one phenyl group, 1–3 alkyl groups of respectively 1–4 carbon atoms, one chloromethyl, fluoromethyl, trifluoromethyl, carboxy, or hydroxy group.

Conventional methods are employed for the production of compounds of general Formula I with a 9-oxo group by the oxidation of the 9-hydroxy group. For example, the oxidation can be effected, while intermediarily masking the 11-and 15-hydroxy groups by silylation (Chem. Comm. [1972], 1120), with the aid of the Jones reagent (J. Chem. Soc. [1953], 2555). The reaction is carried out in a slight excess of the oxidizing agent in a suitable diluent, such as acetone, at temperatures of between 0° C. and −50° C., preferably at −20° C. The reaction is generally terminated after about 5–20 minutes. Excess oxidizing agent is decomposed by adding a lower alcohol, particularly isopropyl alcohol.

Other suitable oxidizing agents are silver carbonate on "Celite" or mixtures of chromium trioxide and pyridine (Tetrahedron Letters 1968, 3363).

The dehydration of the 9-oxo compound ($R_2$ and $R_3$ of Formula I representing an oxygen atom), wherein the 11-hydroxy group and a hydrogen atom are split off from the 10-position, in order to obtain a prostaglandin A-derivative, can be accomplished under conditions generally known to a person skilled in the art. In general, the dehydration is effected in an aqueous solution of an organic acid, such as acetic acid, or in an inorganic acid, such as 0.1N hydrochloric acid, at temperatures of between 20° C. and 80° C. The reaction is terminated after about 2–17 hours.

The hydrogenation of the 13,14- and/or 5,6-double bond is conducted in a manner known per se in a hydrogen atmosphere in the presence of a noble metal catalyst. A suitable catalyst, for example, is 10% palladium on charcoal. If the hydrogenation is carried out at room temperature, the 5,6- as well as the 13,14-double bonds can be saturated. At low temperatures, preferably at −80° C. to −10° C., the cis-5,6-double bond can be hydrogenated before the trans-13,14-double bond. A selective reduction of the cis-5,6-double bond with the simultaneous presence of a trans-13,14-double bond is also accomplished with the catalyst nickel boride or tris(triphenylphosphine)rhodium(I) chloride.

The prostaglandin derivatives of general Formula I with $R_1$ repesenting a carboxy group can be converted into salts with suitable quantities of the corresponding inorganic bases, under neutralization. For example, the solid inorganic salt is obtained when dissolving the corresponding PG acids in water containing the stoichiometric amount of the base, after the water has been evaporated or after the addition of a water-miscible solvent, e.g. alcohol or acetone.

To produce an amine salt, the PG acid is dissolved in a suitable solvent, for example ethanol, acetone, diethyl ether, or benzene, and at least the stoichiometric amount of the amine is added to this solution. The salt is ordinarily obtained in the solid form during this process.

The steps following the main reaction (a), such as esterification, oxidation, and hydrogenation can also be conducted on the bis(tetrahydropyranyl) ether of general Formula II.

In addition to the compounds of general Formula I, the present invention also includes the novel intermediate products of general Formula II, III, and IV.

The intermediates II, III, and IV are prepared in accordance with conventional methods, e.g. in the following way:

Starting with an aldehyde A (E.J. Corey et al., J. Amer. Chem. Soc. 91 [1969] 5675), by Wittig reaction with a phosphorane of the general formula

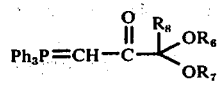

or with a phosphonate of the general formula

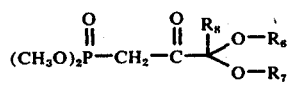

the unsaturated ketone B is obtained.

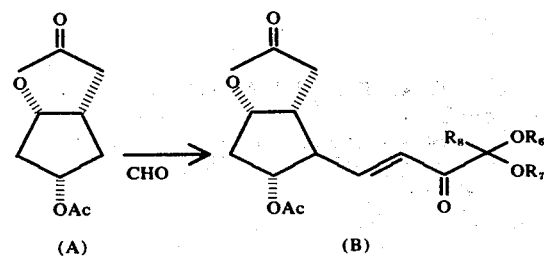

Ac represents an aliphatic or aromatic acyl group and $R_6$, $R_7$, and $R_8$ have the meanings indicated in Formulae I–IV.

The reaction with the phosphorane is conducted in solvents, such as benzene, diethyl ether, tetrahydrofuran, etc., at temperatures of 0°–80° C.

With the use of a phosphonate, the reaction is carried out in the presence of butyllithium or sodium hydride in tetrahydrofuran at temperatures of between 0° C. and −70° C.

The ketone B is reduced to a mixture of the epimeric 15α- and 15β-alcohols III (the numbering corresponds to that in case of the prostaglandin).

The reduction of the 15-oxo group is conducted in an organic solvent with zinc borohydride. Suitable organic solvents are, for example, dimethoxyethane, diethyl ether, dioxane, benzene, isopropyl ether, and mixtures thereof. The separation of the less polar 15α-alcohol from the 15β-alcohol can be accomplished by conventional methods, such as chromatography and/or fractional crystallization. The 15α-configuration is ascribed to the less polar alcohol. The 15α-hydroxy group has the R-configuration and the 15β-hydroxy group has the S-configuration.

Depending on the meaning of A in Formulae III and IV, the 13,14-double bond can also be hydrogenated. The hydrogenation is conducted in the presence of noble metal catalysts, e.g. 10% palladium on charcoal, in an inert diluent, such as methanol or ethyl acetate at room temperature and under normal pressure.

The reduction of ketone B and the optionally following hydrogenation of the 13,14-double bond to obtain compound III will be explained with the aid of the following reaction scheme:

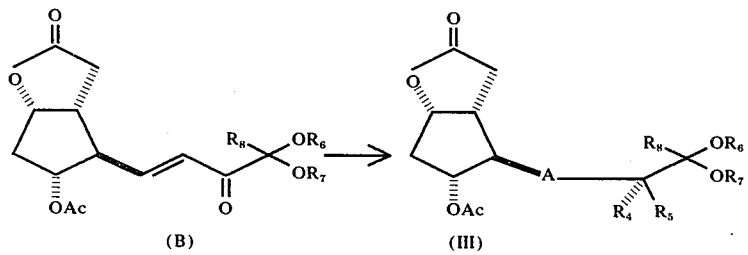

$R_4$ and $R_5$ are different and one is a hydrogen atom and the other hydroxy.

To prepare the compounds of general Formula II, the compounds of general Formula III are first deacylated with an alkali metal carbonate, e.g. potassium carbonate, in methanol at about 25° C.; then, the 11- and 15-hydroxy groups are converted into the bis(tetrahydropyranyl) ethers with the use of dihydropyran, the lactone ring is reduced with diisobutylaluminum hydride at −120° C. to −30° C., and the thus-obtained lactol is reacted with the Wittig reagent of Formula V

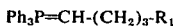

$Ph_3P=CH-(CH_2)_3-R_1$     V to produce the compound of Formula II.

Depending on the significance of A, B, $R_1$, $R_2$, and $R_3$ in Formula II, this reaction can be followed by a hydrogenation of the double bonds, oxidation of the 9-hydroxy group, and esterification of the 1-carboxy group.

The intermediate stages formed from Formula III to Formula II can be explained by the following scheme:

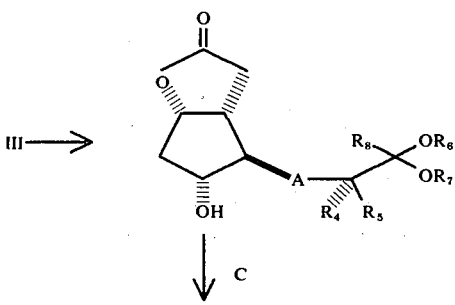

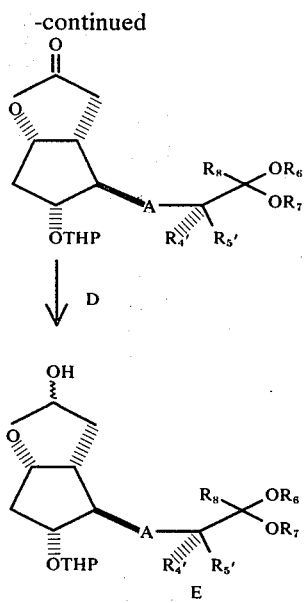

in which $R_4$ and $R_5$ are different and one is hydrogen and one hydroxy. $R_4'$ and $R_5'$ are likewise different and signify hydrogen and OTHP.

THP represents the tetrahydropyranyl group.

The bis(tetrahydropyranyl) ether D is obtained from C with dihydropyran in an inert solvent, e.g. methylene chloride, with the use of an acidic condensation agent, such as p-toluenesulfonic acid. The dihydropyran is used in an excess, preferably four to ten times the amount which is theoretically required. The reaction is normally finished at 20–30° C. after 15–30 minutes.

The lactol E is produced by reducing the lactone D with diisobutylaluminum hydride in an inert solvent, such as hexane, toluene, glyme, diethyl ether, or tetrahydrofuran at low temperatures, approximately between −120° C. and −30° C.

The compounds of general Formula II are obtained by reacting the lactol E with the Wittig reagent of general Formula V. The Wittig reaction is conducted in an aprotic solvent, such as dimethyl sulfoxide or dimethylformamide at temperatures of between 0° C. and 100° C., preferably between 30° C. and 80° C. The Wittig reagent can also be liberated during the reaction from 4-$R_1$-butyltriphenylphosphonium bromide with sodium hydride, potassium tert.-butylate, or butyllithium.

The novel prostaglandin analogs of general Formula I of this invention are valuable pharmaceuticals, since they exhibit, with the same spectrum of activity, a substantially increased and, above all, also essentially prolonged effectiveness as compared to the corresponding natural prostaglandins.

The novel prostaglandin analogs of the E-, D-, and F-type have a very strong luteolytic effect, i.e. to trigger a luteolynsis substantially lower doses are required than in case of the corresponding original prostaglandins.

Also for triggering abortions, essentially lower quantities of the novel prostaglandin analogs are necessary as compared to the original prostaglandins.

In the registration of the isotonic uterus contraction on narcotized rats and on the isolated rat uterus, it is found that the compounds of this invention are substantially more effective and the duration of activity is longer than in the natural prostaglandins.

The novel prostanoic acid derivatives are suitable, after a one-time intrauterine application, to induce menstruation or to interrupt a pregnancy. They are furthermore suitable for synchronizing the conception cycle in female mammals, such as monkeys, rabbits, cattle, pigs, etc.

The satisfactory activity dissociation of the substances of this invention, especially the 16,16-naphthylene-2,3-dioxy derivatives, is demonstrated when examined on other smooth-muscular organs, such as, for example, on the ileum of the guinea pig or on the isolated rabbin trachea, where a substantially lesser stimulation can be observed than effected by the natural prostaglandins.

The active agents of this invention pertaining to the PG E-series show, on the isolated rabbit trachea in vitro, a bronchodilatative effect and strongly inhibit the gastric acid secretion; also, they exert a regulating effect in case of cardiac dysrhythmias. The novel compounds of the PG A- and PG E-series furthermore lower the blood pressure and have a diuretic effect.

The active agents of the F-series, as produced according to this invention, have a lesser bronchoconstrictive effect than natural prostaglandin $F_2$, which is of great advantage for their therapeutic application. For medical administration, the effective agents can be converted into a form suitable for inhalation, or for oral or parenteral application. For inhaling purposes, aerosol or spray solutions are suitably prepared.

For oral application, tablets, dragees, or capsules are suitable, for example.

Sterile, injectable, aqueous or oily solutions are used for parenteral administration.

Accordingly, this invention also relates to medicinal agents on the basis of the compounds of general Formula I and customary auxiliary agents and vehicles.

The active agents of this invention are employed, in conjunction with the auxiliary agents known and customary in galenic pharmacy, for the production of preparations to trigger abortion, to control the cycle, or to induce labor. For this purpose, it is possible to employ sterile, aqueous solutions containing 0.01–100 μg./ml. of the active compound.

To produce aqueous isotonic solutions, the acids and salts of general Formula I are especially suitable. To increase solubility, it is possible to add alcohols, such as ethanol and ethylene glycol.

To trigger abortions 1–10 mg of a PGE-derivative or 10–100 mg of a PGF-derivative are administered once intrauterine or 1–10 mg of a PGE-derivative per minute or 10–100 mg of a PGF-derivative per minute in the form of an intravenous infusion up to 48 hours.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(5Z,13E)-(8R,9S,11R,12R,15R)-9,11,15-Trihydroxy-15-(1,3-dioxa-2-indanyl)-16,17,18,19,20-pentanor-prostadienoic acid

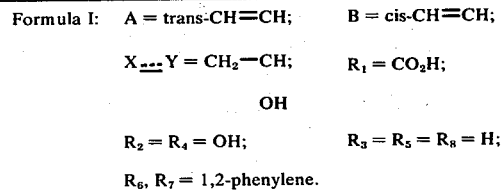

Formula I:  $A = \text{trans-CH}=\text{CH}$;  $B = \text{cis-CH}=\text{CH}$;

$X \cdots Y = CH_2-CH$;  $R_1 = CO_2H$;

OH $R_2 = R_4 = OH$;  $R_3 = R_5 = R_8 = H$;

$R_6, R_7 = 1,2$-phenylene.

100 mg. of (5Z,13E)-(8R,9S, 11R,12R,15R)-9-hydroxy-11,15-bis(tetrahydropyranyloxy)-15-(1,3-dioxa-2-indanyl)-16,17,18,19,20-pentanor-prostadienoic acid was agitated for 3 hours at 45° C. in 3 ml. of a mixture of acetic acid/water/tetrahydrofuran (65/35/10) and then evaporated under vacuum. After column chromatography on 5 g. of silica gel (solvent: chloroform/ethanol = 4 + 1), 60 mg. of the above trihydroxyprostadienoic acid was obtained as a colorless oil.

IR: 3600–3300, 1710, 1500, 980 cm$^{-1}$

TLC (benzene/dioxane/glacial acetic acid = 20/20/1): Rf value = 0.28.

The starting compound for the above substance was prepared as follows:

a.
3-Phenylenedioxyacetonylidenetriphenylphosphorane

At room temperature, 102 ml. of a 1.9-molar butyllithium solution in hexane was added dropwise to a suspension of 69 g. of triphenylmethylphosphonium bromide in 1 liter of absolute ether, and the mixture was stirred for 14 hours under argon. To the yellow solution was added dropwise 34.5 g. of the methyl ester of 1,3-benzodioxole-2-carboxylic acid (Chemical Abstr. 62, p. 564 b), dissolved in 250 ml. of absolute ether. The mixture was agitated for 30 minutes at room temperature and then evaporated to dryness under vacuum. The residue was heated with 1 l. of ethyl acetate to the boiling point, filtered, extracted with water, and dried. The crystalline residue of the evaporating step was recrystallized from ethyl acetate, thus obtaining 21 g. of the phosphorane, m.p. 163°–165° C.

Dimethyl-2-oxo-2-(1,3-dioxa-2-indanyl)-ethylphosphonate

At −70° C., 76 ml. of a 2-molar butyllithium solution in hexane was added dropwise under an argon atmosphere to a solution of 18.8 g. of dimethylmethylphosphonate in 150 ml. of absolute tetrahydrofuran. After 10 minutes, this mixture was combined dropwise with a solution of 14.4 g. of 1,3-benzodioxole-2-carboxylic acid ethyl ester in 20 ml. of absolute tetrahydrofuran. Subsequently, the reaction mixture was agitated for 2 hours at −70° C., neutralized with acetic acid, and concentrated under vacuum. The residue was distributed between 100 ml. of ether and 20 ml. of water, the ether phase was dried over MgSO$_4$, and the liquid residue, after evaporating the ether, was distilled under vacuum, thus producing 9 g. of a colorless oil; b.p. $_{0.1}$ 165° C. (air bath temperature).

b.
(1S,5R,6R,7R)-6-[(E)-3-Oxo-3-(1,3-dioxa-2-indanyl)-1-propenyl]-7-benzoyloxy-2-oxabicyclo[3,3,0]octan-3-one Formula B: $R_6, R_7$ = 1,2-phenylene; $R_8$ = H 1.4 g. of (1S,5R,6R,7R)-6-formyl-7-benzoyloxy-2-oxabicyclo[3,3,0]octan-3-one (E. J. Corey et al., J. Amer. Chem. Soc. 91, 5675 [1969]) and 2.25 g. of 3-phenylenedioxyacetonylidenetriphenylphosphorane were agitated in 50 ml. of benzene under argon for 16 hours at room temperature. The mixture was then evaporated under vacuum. Purification by column chromatography on silica gel (ether/hexane = 8 + 2) and recrystallization from isopropyl ether/methylene chloride yielded 1.18 g. of colorless crystals, m.p. 119°–120° C.

By reacting the 6-formyl compound with the corresponding phosphonate, the same product is obtained:

At −70° C., 0.6 ml. of a 2-molar butyllithium solution in hexane was added dropwise to a solution of 299 mg. of dimethyl-2-oxo-2-(1,3-dioxa-2-indanyl)-ethylphosphonate in 6 ml. of absolute dimethoxyethane; the mixture was warmed to room temperature, and 274 mg. of the above-mentioned 6-formyl compound, dissolved in 5 ml. of absolute dimethoxyethane, was added thereto. The reaction mixture was agitated for 1 hour at room temperture. After neutralization with glacial acetic acid, the mixture was combined with water, extracted with ether, shaken with sodium bicarbonate solution and water, dried over magnesium sulfate, and evaporated under vacuum. The residue was recrystallized from isopropyl ether/methylene chloride, thus obtaining 220 mg. of crystals, m.p. 119°–120° C.

c.
(1S,5R,6R,7R,3′R)-6-[(E)-3-Hydroxy-3-(1,3-dioxa-2-indanyl)-1-propenyl]-7-benzoyloxy-2-oxabicyclo[3,3,0]octan-3-one Formula III: A = trans-CH=CH; $R_4$ = OH; $R_5$ = $R_8$ = H; $R_6, R_7$ = 1,2-phenylene A solution of 635 mg. of the ketone obtained according to (b) in 50 ml. of absolute dimethoxyethane was combined with 50 ml. of ethereal zinc borohydride solution (prepared according to "Neuere Methoden der preparativen organischen Chemie" [Newer Methods of Preparative Organic Chemistry], vol. 4, p. 241, publishers: Chemie) and agitated overnight at room temperature. After water had been gently added to the reaction mixture, the latter was diluted with ether, extracted with brine, dried over magnesium sulfate, and evaporated under vacuum. Elution by column chromatography on silica gel (hexane/ether = 3 + 7) yielded first of all 246 mg. of the α-alcohol (title compound) as colorless crystals, m.p. 91°–92° C., as well as 260 mg. of the corresponding β-alcohol (1S,5R,6R,7R,3′S)-6-[(E)-3-hydroxy-2-(1,3-dioxa-2-indanyl)-1-propenyl[-7-benzoyloxy-2-oxabicyclo[3,3,0]octan-3-one as a colorless oil.

d.
(1S,5R,6R,7R,3′R)-6-[(E)-3-Hydroxy-3-(1,3-dioxa-2-indanyl)-1-propenyl]-7-hydroxy-2-oxabicyclo[3,3,0]octan-3-one Formula C: A = trans-CH=CH; $R_4$ = OH; $R_5$ = $R_8$ = H; $R_6, R_7$ = 1,2-phenylene 293 mg. of anhydrous potassium carbonate was added to a solution of 895 mg. of the α-alcohol obtained according to (c) in 40 ml. of absolute methanol; the mixture was stirred at room temperature for 2 hours under argon; then, 42.4 ml. of 0.1N hydrochloric acid was added thereto. The solution was diluted with brine, extracted with ethyl acetate, shaken with brine, dried over magnesium sulfate, and evaporated to dryness under vacuum. The residue was chromatographed on silica gel (ether/ethyl acetate = 7 + 3), thus producing 480 mg. of a colorless oil.

TLC (ether/dioxane = 9 + 1): Rf value = 0.25.

e.
(1S,5R,6R,7R,3′R)-6-[(E)-3-(1,3-Dioxa-2-indanyl)-1-propenyl]-3′,7-bis(tetrahydropyranyloxy)-2-oxabicyclo[3,3,0]octan-3-one Formula D: A = trans-CH=CH; $R_4'$ = OTHP; $R_5'$ = $R_8$ = H; $R_6, R_7$ = 1,2-phenylene 460 mg. of the diol obtained according to (d), 1.2 ml. of freshly distilled dihydropyran, 22 mg. of p-toluenesulfonic acid in 11 ml. of absolute methylene chloride was agitated for 15 minutes at room temperature under argon. After dilution with methylene chloride, the mixture was extracted with sodium bicarbonate solution and water, dried over magnesium sulfate, and evaporated to dryness under vacuum. After filtration of the residue over a small amount of silica gel (ether/hexane = 7 + 3), 586 mg. of bis(tetrahydropyranyl) ether was obtained as colorless crystals, m.p. 99°–101° C. TLC (ether): Rf value = 0.4.

f.
(2RS,3aR,4R,5R,6aS,3′R)-4-[(E)-3-(1,3-Dioxa-2-indanyl)-1-propenyl]-2-hydroxy-3′,5-bis(tetrahydropyranyloxy)perhydrocyclopenta[b]furan Formula E: A = trans-CH=CH; $R_4'$ = OTHP; $R_5'$ = $R_8$ = H; $R_6, R_7$ = 1,2-phenylene Under argon, 10 ml. of a 20% solution of diisobutylaluminum hydride in toluene was added to a solution, cooled to −60° C., of 1.28 g. of the lactone bis(tetrahydropyranyl) ether produced according to (e) in 50 ml. of absolute toluene. The mixture was stirred for 30 minutes at −60° C., and the reaction was terminated by the dropwise addition of 3 ml. of isopropanol. After adding 50 ml. of water, the mixture was agitated for 15 minutes at 0° C., extracted with ethyl acetate, dried over magnesium sulfate, and evaporated and dried under vacuum thus obtaining 1.27 g. of the above-mentioned lactol as a colorless oil. TLC (ether): Rf value = 0.35.

g.
(5Z,13E)-(8R,9S,11R,12R,15R)-9-Hydroxy-11,15-bis(tetrahydropyranyloxy)-15-(1,3-dioxa-2-indanyl)-16,17,18,19,20-pentanor-prostadienoic Acid Formula II: A = trans-CH=CH; R₄' = OTHP; R₂ = OH; R₅' = R₈ = H; R₆,R₇ = 1,2-phenylene; R₁ = CO₂H; R₃ = H 9.1 ml. of a solution of methanesulfinylmethylsodium in absolute DMSO (preparation: 0.70 g. of 50% sodium hydride suspension was dissolved in 14 ml. of absolute DMSO at 75° C.) was added to a solution of 2.50 g. of 4-carboxybutyltriphenylphosphonium bromide in 8 ml. of absolute dimethyl sulfoxide (DMSO); the mixture was agitated at room temperature for 30 minutes. To this solution was added dropwise 550 mg. of the lactol obtained in accordance with (f), dissolved in 8 ml. of absolute DMSO, and the mixture was agitated for 2 hours at 50° C. The reaction mixture was then poured on ice water and extracted three times with ether. This ether extract was discarded. The aqueous phase was acidified to pH 4 with 10% strength citric acid and extracted four times with an ether/hexane mixture (1 + 1). The organic phase was extracted with brine, dried over magnesium sulfate, and evaporated under vacuum. Chromatography of the residue on silica gel (ether) yielded 430 mg. of the above-mentioned prostadienoic acid as a colorless oil.

TLC (chloroform/tetrahydrofuran/acetic acid = 10/2/1): Rf value = 0.51.

EXAMPLE 2

(5Z,13E)-(8R,9S,11R,12R,15S)-9,11,15-Trihydroxy-15-(1,3-dioxa-2-indanyl)-16,17,18,19,20-pentanor-prostadienoic Acid

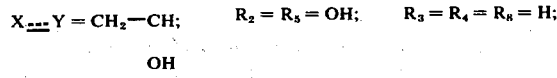

Formula I:  A = trans-CH=CH;   B = cis-CH=CH;

X⋯Y = CH₂—CH;   R₂ = R₅ = OH;   R₃ = R₄ = R₈ = H;

OH

R₆, R₇ = 1,2-phenylene;   R₁ = CO₂H 110 mg. of (5Z,13E)-(8R,9S,11R,12R,15S)-9-hydroxy-11,15-bis(tetrahydropyranyloxy)-15-(1,3-dioxa-2-indanyl)-16,17,18,19,20-pentanor-prostadienoic acid was agitated for 3 hours at 50° C. in 3 ml. of a mixture of acetic acid/water/tetrahydrofuran = 65/35/10 and evaporated to dryness under vacuum. After chromatography on 5 g. of silica gel (chloroform/ethanol = 4 + 1), 63 mg. of the above trihydroxyprostadienoic acid was obtained as a colorless oil.

IR: 3600–3300 wide, 1710, 1500, 980 cm⁻¹

TLC (benzene/dioxane/glacial acetic acid = 20/20/1): Rf value = 0.31.

The starting material was produced as follows:

a.
(1S,5R,6R,7R,3'S)-6-[(E)-3-Hydroxy-3-(1,3-dioxa-2-indanyl)-1-propenyl]-7-hydroxy-2-oxabicyclo-[3,3,0]octan-3-one Formula C: A = trans-CH=CH; R₄ = R₈ = H; R₅ = OH; R₆,R₇ = 1,2-phenylene 1.24 g. of the β-alcohol obtained according to Example 1 (c) and 405 mg. of anhydrous potassium carbonate was stirred in 50 ml. of absolute methanol for 2 hours at room temperature and under an argon atmosphre. Then, 58 ml. of 0.1N HCl was added thereto, the mixture was diluted with brine, extracted with ethyl acetate, the extract shaken with brine, dried over magnesium sulfate, and evaporated to dryness under vacuum. Chromatography of the residue on silica gel (ether/ethyl acetate = 7 + 3) yielded 740 mg. of the diol in the form of a colorless oil.

TLC (ether/dioxane = 8 + 2): Rf value = 0.52.

(b)
(1S,5R,6R,7R,3'S)-6-[(E)-3-(1,3-Dioxa-2-indanyl)-1]-3',7-bis(tetrahydropyranyloxy)-2-oxabicyclo[3,3,0]octan-3-one Formula D: A = trans-HC=CH; R₄' = R₈ = H; R₅' = OTHP; R₆,R₇ = 1,2-phenylene According to Example 1 (e), 700 mg. of the above bis-(tetrahydropyranyl) ether was obtained from 717 mg. of the lactone produced according to Example 2 (a).

TLC (ether): Rf value = 0.34.

(c)
(2RS,3aR,4R,5R,6aS,3'S)-4-[(E)-3-(1,3-Dioxa-2-indanyl)-1-propenyl]-2-hydroxy-3',5-bis(tetrahydropyranyloxy)perhydrocyclopenta[b]furan Formula E: A = trans-CH=CH; R₄' = R₈ = H; R₅' = OTHP; R₆,R₇ = 1,2-phenylene According to Example 1 (f), 515 mg. of the above lactol was produced from 520 mg. of the bis(tetrahydropyranyl) ether obtained in accordance with Example 2(b).

TLC (ether)- Rf value = 0.28.

d. (5Z,13E)-(8R,9S,11R, 12R, 15S)-9-Hydroxy-11,15-bis(tetrahydropyranyloxy)-15-(1,3-dioxa-2-indanyl)-16, 17, 18, 19, 20-pentanor-prostadienoic Acid Formula II: A = trans-CH=CH; R₃ = R₄' = R₈ = H; R₅' = OTHP; R₂ = OH; R₆,R₇ = 1,2-phenylene; R₁ = CO₂H According to Example 1 (g), 520 mg. of the lactol obtained according to (c) was converted into 450 mg. of the above-identified prostadienoic acid; colorless oil.

TLC (chloroform/tetrahydrofuran/acetic acid = 10/2/1): Rf value = 0.55.

EXAMPLE 3

(5Z)-(8R,9S,11R,12R,15R)-9,11,15-Trihydroxy-15-(1,3-dioxa-2-indanyl)-16,17,18,19,20-pentanor-prostenoic Acid Formula I:   A = CH₂—CH₂;   B = cis-CH=CH;

| -continued |
|---|
| X---Y = CH$_2$—CH;    R$_1$ = CO$_2$H |
| OH |
| R$_2$ = R$_4$ = OH;    R$_3$ = R$_5$ = R$_8$ = H; |
| R$_6$, R$_7$ = 1,2-phenylene |

300 mg. of (5Z)-(8R,9S,11R,12R,15R)-9-hydroxy-11,15-bis(tetrahydropyranyloxy)-15-(1,3-dioxa-2-indanyl)-16,17,18,19,-20-pentanor-prostenoic acid was agitated in 9 ml. of a mixture of acetic acid/water/tetrahyrofuran = 65/35/10 for 3 hours at 50° C. The mixture was evaporated to dryness under vacuum. Chromatography on 10 g. of silica gel (chloroform/ethanol = 4 + 1) yielded 204 mg. of the above-identified compound as a colorless oil.

IR: 3600–3300, 1710, 1500 cm$^{-1}$
TLC (benzene/dioxane/glacial acetic acid = 20/20/1): Rf value = 0.30.

The starting material was produced as follows:

a. (1S,5R,6R,7R,3′R)-6-[3-Hydroxy-3-(1,3-dioxa-2-indanyl)-1-propyl]-7-benzoyloxy-2-oxabicyclo-[3,3,0]octan-3-one Formula III: A = CH$_2$-CH$_2$; R$_4$ = OH; R$_5$ = R$_8$ = H; R$_6$,R$_7$ = 1,2-phenylene 4.5 g. of the α-alcohol obtained according to Example 1 (c) and 450 mg. of palladium on charcoal (10% strength) were shaken for 2 hours in 80 ml. of ethyl acetate under a hydrogen atmosphere. After filtration and evaporation, 4.5 g. of the above alcohol was obtained as a colorless oil.

IR: 3600, 1775, 1720, 1500 cm$^{-1}$
TLC (ether): Rf value = 0.17.

No olefinic protons could be observed in the NMR spectrum.

b. (1S,5R,6R,7R,3′R)-6-[3-Hydroxy-3-(1,3-dioxa-2-indanyl)-1-propyl]-7-hydroxy-2-oxabicyclo [3,3,0]-octan-3-one Formula C: A =: CH$_2$-CH$_2$; R$_4$ = OH R$_5$ = R$_8$ = H; R$_6$,R$_7$ = 1,2-phenylene by interesterification according to Example 1 (d), 1.46 g. of the saturated diol was obtained as a colorless oil from 2.40 g. of the saturated alcohol obtained according to (a).

IR: 3600 strong, 1775, 1500 cm$^{-1}$
TLC (ether/dioxane = 9 + 1): Rf value = 0.27.

c. (1 S, 5R,6R,7R,3′R)-6-[3-(1,3-Dioxa-2-indanyl)-1-propyl]-3′,7-bis(tetrahydropyranyloxy)-2-oxabicyclo[3,3,-0]octan3-one Formula D: A = CH$_2$-CH$_2$; R$_4$′ = OTHP; R$_5$′ = R$_8$ = H; R$_6$,R$_7$ = 1,2-phenylene With dihydropyran, 1.05 g. of the above bis(tetrahydropyranyl) ether is obtained as a colorless oil analogously to Example 1(e) from 1.10 g. of the diol produced according to (b).

IR: 1775, 1500, 1100 cm$^{-1}$
TLC (ether): Rf value = 0.35.

d. (2RS,3aR,4R,5R,6aS,3′R)-4-[3-(1,3-Dioxa-2-indanyl)-1-propyl]-2-hydroxy-3′,5-bis-(tetrahydropyranyloxy)-perhydrocyclopenta[b] furan Formula E: A = CH$_2$-CH$_2$; R$_4$′ = OTHP; R$_5$′ = R$_8$ H; R$_6$,R$_7$ = 1,2-phenylene According to Example (1 (f), 1.03 g. of the above lactol was produced as a colorless oil by the reduction of 1.05 g. of the bis(tetrahydropyranyl) ether prepared according to (c).

IR: 3600, 1500, 1100 cm$^{-1}$
TLC (ether): Rf value = 0.37.

e. (5Z)-(8R,9S,11R,12R,15R)-9-Hydroxy-11,15-bis-(tetrahydropyranyloxy)-15-(1,3-dioxa-2-indanyl)-16,17,18,19,20-pentanor-prostenoic Acid Formula II: A = CH$_2$-CH$_2$; R$_1$ = CO$_2$H; R$_3$ = R$_5$′ = R$_8$ = H; R$_2$ = OH; R$_4$′ = OTHP R$_6$,R$_7$= 1,2-phenylene 1.03 g. of the lactol obtained according to (d) was converted as described in Example 1(g) into 832 mg. of the above-identified prostenoic acid.

IR: 3600–3400, 1710, 1500, 1100 cm$^{-1}$
TLC (chloroform/tetrahydrofuran/acetic acid = 20/4/2): Rf value = 0.50.

EXAMPLE 4

(5Z)-(8R,9S,11R,12R,15S)-9,11,15-Trihydroxy-15-(1,3-dioxa-2-indanyl)-16,17,18,19,20-pentanor-prostenoc Acid

| Formula I: | A = CH$_2$—CH$_2$; | B = cis-CH=CH; | X---Y = CH$_2$—CH; |
|---|---|---|---|
| | | | OH |
| | R$_1$ = CO$_2$H; | R$_2$ = R$_5$ = OH; | R$_3$ = R$_4$ = H; |
| | R$_6$, R$_7$ = 1,2-phenylene; | R$_8$ = H | |

According to Example 3, 212 mg. of the above compound was obtained as a colorless oil from 334 mg. of (5Z)-(8R,9S,-11R,12R,15S)-9-hydroxy-11,15-bis(tetrahydropyranyloxy)-15-(1,3-dioxa-2-indanyl)-16,17,18,19,20-pentanor-prostenoic acid.

IR: 3600–3300, 1710, 1500 cm$^{-1}$
TLC (benzene/dioxane/glacial acetic acid = 20/20/1): Rf value = 0.31.

The starting material was produced as follows:

a.
(1S,5R,6R,7R,3′S)-6-[3-Hydroxy-3-(1,3-dioxa-2-indanyl)-1-propyl]-7-benzoyloxy-2-oxabicyclo[3,3,0]octan-3one Formula III: A = -CH$_2$-CH$_2$-; R$_5$ = OH R$_4$ = R$_8$ = H
R$_6$,R$_7$ = 1,2-phenylene Analogously to Example 3(a), 2.4 g. of the β-alcohol obtained according to Example 1(c) was hydrogenated to 2.4 g. of the above-mentioned saturated alcohol, obtained as a colorless oil.
IR: 3600, 1775, 1720, 1500 cm$^{-1}$
TLC (ether): Rf value = 0.18.

b.
(1S,5R,6R,7R,3′S)-6-[3-Hydroxy-3-(1,3-dioxa-2-indanyl)-1-propyl]-7-hydroxy-2-oxabicyclo[3,3,0]-octan-3-one Formula C: A = CH$_2$-CH$_2$; R$_4$ = R$_8$ = H; R$_5$ = OH;
R$_6$,R$_7$ = 1,2-phenylene By interesterification with potassium carbonate according to Example 1(d), 1.15 g. of the saturated diol is obtained as a colorless oil from 1.9 g. of the saturated alcohol produced in accordance with (a).
IR: 3600 strong, 1775, 1500 cm$^{-1}$
TLC (ether/dioxane = 9 + 1): Rf value = 0.29.

c.
1S,5R,6R,7R,3′S)-6-[3-(1,3-Dioxa-2-indanyl)-1-propyl]-3′,7-bis(tetrahydropyranyloxy)-2-oxabicyclo[3;3,0]octan-3-one Formula D: A = CH$_2$-CH$_2$; R$_4$′ = R$_8$ = H; R$_5$′ = OTHP; R$_6$,R$_7$ = 1,2-phenylene From 0.96 g. of the diol produced according to (b), 0.90 g. of the above bis(tetrahydropyranyl) ether was obtained with dihydropyran analogously to Example 1(e) as colorless oil.
IR: 1775, 1500, 1100 cm$^{116\ 1}$
TLC (ether): Rf value = 0.38.

d.
(2RS,3aR,4R,5R,6aS,3′S)-4-[3-(1,3-Dioxa-2-indanyl)-1-propyl]-2-hydroxy-3′,5-bis(tetrahydropyranyloxy)-perhydrocyclopenta[b]furan Formula E: A = CH$_2$-CH$_2$; R$_4$′ = R$_8$ = H; R$_5$′ = OTHP; R$_6$,R$_7$ = 1,2-phenylene According to Example 1(f), 0.7 g. of the above lactol was produced as a colorless oil by the reduction of 0.74 g. of the bis(tetrahydropyranyl) ether prepared according to (c).
IR: 3600, 1500, 1100 cm$^{-1}$
TLC (ether): Rf value = 0.41.

e.
(5Z)-(8R,9S,11R,12R,15S)-9-Hydroxy-11,15-bis(tetrahydropyranyloxy)15-(1,3-dioxa-2-indanyl)-16,17,18,19,20-pentanor-prostenoic Acid Formula II: A = CH$_2$-CH$_2$; R$_1$ = CO$_2$H; R$_2$ = OH; R$_3$ = R$_4$′ = R$_3$ = H; R$_5$′ = OTHP; R$_6$,R$_7$ = 1,2-phenylene 0.7 g. of the lactol obtained in accordance with (d) was converted, as described in Example 1(g), into 0.51 g. of the aforementioned prostenoic acid.
IR: 3600–3400, 1710, 1500, 1100 cm$^{-1}$
TLC (chloroform/tetrahydrofuran/acetic acid = 10/2/1): Rf value = 0.52.

EXAMPLE 5

(2RS,3aR,4R,5R,6aS,3′R)-4-[(E)-3-Hydroxy-3-(1,3-dioxa-2-indanyl)-1-propenyl]-2,5-dihydroxyperhydrocyclopenta[b]furan Formula IV: A = trans-CH=CH; R$_4$ = OH; R$_5$ = R$_8$ = H; R$_6$,R$_7$ = 1,2-phenylene Under argon, 5 ml. of a 20% diisobutylaluminum hydride solution in toluene was added dropwise to a solution, cooled to −60° C., of 433 mg. of the α-alcohol obtained according to Example 1(c) in 30 ml. of absolute toluene. The mixture was then stirred for 30 minutes, and the reaction was terminated by the dropwise addition of 1 ml. of isopropanol. After adding 20 ml. of water, the mixture was agitated for 15 minutes at 0° C., extracted with ethyl acetate, shaken with brine, dried over magnesium sulfate, and evaporated to dryness under vacuum. After chromatography on 5 g. of silica gel (ether/dioxane = 8 + 2), 314 mg. of the above-mentioned lactol was obtained.
TLC (ether/dioxane = 9 + 1): Rf value = 0.16.

(5Z,13E)-(8R,9S,11R,12R,15R)-9,11,15-Trihydroxy-15-(1,3-dioxa-2-indanyl)-16,17,18,19,20-pentanor-prostadienoic Acid Formula I: A = trans-CH=CH; B = cis-CH=CH;
X---Y = CH$_2$—CH; R$_1$ = CO$_2$H; R$_2$ = R$_4$ = OH;
$$R_3 = R_5 = R_8 = H;\quad R_6, R_7 = 1,2\text{-phenylene}$$
(with OH on R$_4$)

13 ml. of a solution of a methanesulfinylmethylsodium in absolute DMSO (produced according to Example 1[g]) was added to a solution of 3.15 g. of 4-carboxybutyltriphenylphosphonium bromide in 9 ml. of absolute DMSO; the mixture was stirred for 30 minutes at room temperature. To this solution was added dropwise 314 mg. of (2RS, 3aR, 4R,5R,6aS,3′R)-4-[(E)-3-hydroxy-3-(1,3-dioxa-2-indanyl)-1-propenyl]-2,5-dihydroxyperhydrocyclopenta[b] furan, dissolved in 5 ml. of absolute DMSO, and the mixture was agitated for 2 hours at 50° C. The mixture was then poured on ice water and extracted three times with ether. The aqueous phase was acidified with 10% citric acid solution to pH 4, extracted with methylene chloride, the methylene chloride phase was shaken with brine, dried over magnesium sulfate, and evaporated to dryness under vacuum. After chromatography of the residue on silica gel, 250 mg. of the above prostadienoic acid was acid was eluted with chloroform/methanol (4 + 1) as a colorless oil. The substance proved to be identical to the compound obtained in accordance with Example 1.

EXAMPLE 6

(2RS,3aR,4R,5R,6aS,3′S)-4-[(E)-3-Hydroxy-3-(1,3-dioxa-2-indanyl)-1-propenyl]-2,5-dihydroxyperhydrocyclopenta[b]furan Formula IV: A = trans-CH=Ch; $R_4 = R_8 = H$; $R_5 =$ OH; $R_6, R_7 = $ 1,2-phenylene From 560 mg. of the β-alcohol produced according to Example 1(c), 415 mg. of the above lactol was obtained by proceeding as set forth in Example 5.

TLC (ether/dioxane = 9 + 1): Rf value = 0.18.

(5Z,13E)-(8R,9S,11R,12R,15S)-9,11,15-Trihydroxy-15-(1,3-dioxa-2-indanyl)-16,17,18,19,20-pentanor-prostadienoic Acid

| Formula I: | A = trans-CH=CH; | B = cis-CH=CH; | X⋯Y = CH$_2$—CH; |
| --- | --- | --- | --- |
| | | | OH |
| | $R_2 = R_5$ = OH; | $R_3 = R_4 = R_8$ = H; | |
| | $R_6, R_7$ = 1,2-phenylene; | $R_1 = CO_2H$ | |

According to Example 5, 410 mg. of (2RS,3aR,4R,5R,-6aS,3′S)-4-[(E)-3-hydroxy-3-(1,3-dioxa-2-indanyl)-1-propenyl]-2,5-dihydroxyperhydrocyclopenta[b]furan was converted into 280 mg. of the above compound, conforming in all of its properties with the compound obtained in accordance with Example 2.

EXAMPLE 7

(5Z,13E)-(8R,11R,12R,15R)-11,15-Dihydroxy-9-oxo-15-(1,3-dioxa-2-indanyl)-16,17,18,19,20-pentanor-prostadienoic Acid

| Formula I: | A = trans-CH=CH; | B = cis-CH=CH; | $R_1 = CO_2H$; |
| --- | --- | --- | --- |
| | $R_2, R_3$ = O; | X⋯Y = CH$_2$—CH; | $R_5 = R_8$ = H; |
| | | | OH |
| | $R_4$ = OH; | | |
| | $R_6, R_7$ = 1,2-phenylene | | |

A mixture of 420 mg. of (5Z,13E)-(8R,11R,12R,15R)-11,15-bis(tetrahydropyranyloxy)-9-oxo-15-(1,3-dioxa-2-indanyl)-16,17,18,19,20-pentanor-prostadienoic acid and 10 ml. of a solution of acetic acid/water/tetrahydrofuran (65/35/10) was stirred for 5 hours at 38° C. and then evaporated under vacuum. The residue was chromatographed on silica gel (chloroform/ethanol = 95 + 5), thus obtaining 250 mg. of the aforementioned compound as a colorless oil.

IR: 3600–3300, 1740, 1705, 1500, 980 cm$^{-1}$

The starting material for the above compound was prepared as follows:

(5Z,13E)-(8R,11R,12R,15R)-11,15-Bis(tetrahydropyranyloxy)-9-oxo-15-(1,3-dioxa-2-indanyl)-16,17,18,19,20-pentanor-prostadienoic Acid Formula II: A = trans-CH=CH; $R_1 = CO_2H$; $R_2, R_3$ = O; $R_4′$ = OTHP; $R_5′ = R_8$ = H; $R_6, R_7$ = 1,2-phenylene 310 mg. of the substance obtained according to Example 1(g) was dissolved in 7.5 ml. of acetone and combined, at −20° C., with 0.27 ml. of Jones reagent (J. Chem. Soc. 1953, 2555). After 15 minutes, the excess reagent was destroyed by the dropwise addition of 0.37 ml. of isopropanol; the mixture was diluted with 40 ml. of water and extracted three times with methylene chloride. The organic extract was shaken with brine, dried over magnesium sulfate, and concentrated under vacuum, thus obtaining 240 mg. of the aforementioned compound as an oil having a slightly yellow coloring.

IR: 3600–3300, 1740, 1710, 1500, 980 cm$^{-1}$

EXAMPLE 8

(5Z,13E)-(8R,11R,12R,15S)-11,15-Dihydroxy-9-oxo-15-(1,3-dioxa-2-indanyl)-16,17,18,19,20-pentanor-prostadienoic Acid

| Formula I: | A = trans-CH=CH; | B = cis-CH=CH; | $R_1 = CO_2H$; |
| --- | --- | --- | --- |
| | $R_2, R_3$ = O; | X⋯Y = CH$_2$—CH; | $R_4 = R_8$ = H; |
| | | OH | |
| | $R_5$ = OH; | $R_6, R_7$ = 1,2-phenylene | |

According to Example 7, 95 mg. of the above-mentioned compound was obtained as a colorless oil from 180 mg. of (5Z,13E)-(8R,11R,12R,15S)-11,15-bis(tetrahydropyranyloxy)-9-oxo-15-(1,3-dioxa-2-indanyl)-16,17,18,19,20-pentanor-prostadienoic acid.

IR: 3600–3300, 1740, 1705, 1500, 980 cm$^{-1}$

TLC (chloroform/tetrahydrofuran/glacial acetic acid = 200/40/20): Rf value = 0.39.

The starting substance for the above compound was produced as follows:

(5Z,13E)-(8R,11R,12R,15S)-11,15-Bis(tetrahydropyranyloxy)-9-oxo-15-(1,3-dioxa-2-indanyl)-16,17,18,19,20-pentanor-prostadienoic Acid Formula II: A= trans-CH=CH; $R_1 = CO_2H$; $R_2, R_3$ = O; $R_4′ = R_8$ = H; $R_5′$ = OTHP; $R_6, R_7$ = 1,2-phenylene 500 mg. of the compound obtained according to Example 2(d) was converted by oxidation analogously to Example 7(a) into 390 mg. of the aforementioned compound.

IR: 3600–3300, 1740, 1710, 1500, 980 cm$^{-1}$

EXAMPLE 9

(5Z)-(8R,11R,12R,15R)-11,15-Dihydroxy-9-oxo-15-(1,3-dioxa-2-indanyl-16,17,18,19,20-pentanor-prostenoic Acid

| Formula I: | A = CH$_2$—CH$_2$; | B = cis-CH=CH; | X---Y = CH$_2$—CH; |
| --- | --- | --- | --- |
| | | | OH |
| | R$_2$, R$_3$ = O; | R$_4$ = OH; | |
| | R$_5$ = R$_8$ = H; | R$_6$, R$_7$ = 1,2-phenylene | |

According to Example 7, 75 mg. of the above compound was obtained as a colorless oil from 135 mg. of (5Z)-(8R,11R,12R,15R)-11,15-bis(tetrahydropyranyloxy)-9-oxo-15-(1,3-dioxa-2-indanyl)-16,17,18,19,20-penatanor-prostenoic acid.

IR: 3600–3300, 1740, 1710, 1500 cm$^{-1}$

The starting material for the above-mentioned compound was prepared as follows:

(5Z)-(8R,11R,12R,15R)-11,15-Bis(tetrahydropyranyloxy)-9-oxo-15-(1,3-dioxa-2-indanyl)-16,17,18,19,20-pentanor-prostenoic Acid Formula II: A = CH$_2$-CH$_2$; R$_1$ = CO$_2$H; R$_2$,R$_3$ =O; R$_4$' = OTHP; R$_5$' = R$_8$ = H; R$_6$,R$_7$ = 1,2-phenylene 286 mg. of the compound obtained according to Example 3(e) was converted into the above compound by oxidation analogously to Example 7(a); yield: 203 mg. of a colorless oil.

IR: 3600–3300, 1740, 1710, 1500 cm$^{-1}$

EXAMPLE 10

(5Z)-(8R,11R,12R,15S)-11,15-Dihydroxy-9-oxo-15-(1,3-dioxa-2-indanyl)-16,17,18,19,20-pentanor-prostenoic Acid

| Formula I: | A = CH$_2$—CH$_2$; B = cis-CH=CH; R$_1$ = CO$_2$H; |
| --- | --- |
| | X---Y = CH$_2$—CH; R$_2$, R$_3$ = O; R$_4$ = R$_8$ = H; |
| | OH |
| | R$_5$ = OH; R$_6$, R$_7$ = 1,2-phenylene |

According to Example 7, 156 mg. of (5Z)-(8R,11R,12R,-15S)-11,15-bis(tetrahydropyranyloxy)-9-oxo-15-(1,3-dioxa-2-indanyl)-16,17,18,19,20-pentanor-prostenoic acid yielded 91 mg. of the above-mentioned compound as a colorless oil.

IR: 3600-3300, 1740, 1710, 1500 cm$^{-1}$

The starting substance for the above compound was produced as described below:

(5Z)-(8R,11R,12R,15S)-11,15-Bis(tetrahydropyranyloxy)-9-oxo-15-(1,3-dioxa-2-indanyl)-16,17,18,19,20-pentanor-prostenoic Acid Formula II: A = CH$_2$-CH$_2$; R$_1$ = CO$_2$H; R$_2$,R$_3$ = O; R$_4$' = R$_8$ = H; R$_5$' = OTHP; R$_6$,R$_7$ = 1,2-phenylene By oxidation according to Example 7(a), 156 mg. of the aforementioned compound was obtained as a colorless oil from 203 mg. of the compound prepared according to Example 4(e).

IR: 3600–3300, 1740, 1710, 1500 cm$^{-1}$

EXAMPLE 11

(5Z,13E)-(8R,9S,11R,12R,15R)-9,11,15-Trihydroxy-16,16-(naphthylene-2,3-dioxy)-17,18,19,20-tetranor-prostadienoic Acid

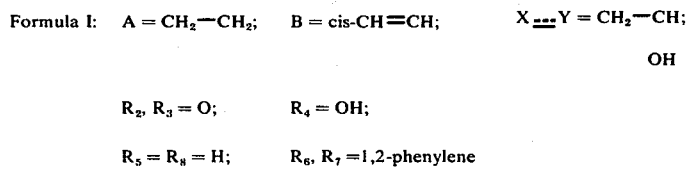

| Formula I: | A = trans-CH=CH; B = cis-CH=CH; |
| --- | --- |
| | X---Y = CH$_2$—CH; R$_2$ = R$_4$ = OH; R$_3$ = R$_5$ = R$_8$ = H; |
| | R$_1$ = CO$_2$H; R$_6$, R$_7$ = |

152 mg. of (5Z,13E)-(8R,9S,11R,12R,15R)-9-hydroxy-11,15-bis(tetrahydropyranyloxy)-16,16-(naphthylene-2,3-dioxy)-17,18,19,20-tetranor-prostadienoic acid was agitated in 3.5 ml. of a mixture of acetic acid/water/tetrahydrofuran (65/35/10) for 3 hours at 50° C. After evaporation and column chromatography on 10 g. of silica gel (chloroform/ethanol = 4 + 1), 73 mg. of the above compound was obtained as a colorless oil.

TLC (chloroform/tetrahydrofuran/acetic acid = 10/2/1): Rf value = 0.19.

The starting product was obtained as follows:

a. 3-(Naphthylene-2,3-dioxy)-actonylidenetriphenylphosphorane

At room temperature, 66 ml. of a 2-molar butyllithium solution in hexane was added dropwise to a suspension of 47.6 g. of triphenylmethylphosphonium bromide in 500 ml. of ether; the mixture was agitated for 14 hours under argon. To the yellow -ylene solution was added gradually and dropwise 36.1 g. of the methyl ester of naphtho[2,3-d]-1,3-dioxole-2-carboxylic acid (m.p. 72° C.; prepared analogously to Chemical Abstracts 62, p. 564b), dissolved in 200 ml. of absolute ether. The mixture was stirred for 60 minutes at room temperature and evaporated to dryness under vacuum. The residue was heated to the boiling point with 0.5 l. of ethyl acetate, filtered, extracted with water, and dried. The crytalline residue of the evaporation was recrystallized from isopropyl ether/methylene chloride, yielding 15.1 g. of the above-mentioned -ylene, m.p. 193° C.

b.
(1S,5R,6R,7R)-6-[(E)-3-Oxo-4,4-(naphthylene-2,3-dioxy)-1-butenyl]-7-benzoyloxy-2-oxabicyclo-[3,3,0]octan-3-one Formula B: $R_6, R_7 =$  ; $R_8 = H$ 1.40 g. of (1S,5R,6R,7R)-6-formyl-7-benzoyloxy-2-oxabicyclo[3,3,0]octan-3-one (see Example 1[b]) and 2.50 g. of 3-(naphthylene-2,3-dioxy)-acetonylidenetriphenylphosphorane were agitated under argon at room temperature for 16 hours in 40 ml. of benzene. The benzene was then distilled off and the residue purified by chromatography on silica gel (ether/hexane = 8 + 2) and recrystallization from isopropyl ether/methylene chloride, yielding 1.15 g. of the above compound as a colorless oil.

c.
(1S,5R,6R,7R,3'R)-6-[(E)-3-Hydroxy-4,4-(naphthylene-2,3-dioxy)-1-butenyl]-7-benzoyloxy-2-oxabicyclo[3,3,0]-octan-3-one Formula III: $A = \text{trans-CH}=\text{CH}$; $R_4 = OH$; $R_5 = R_8 = H$;

$R_6, R_7 =$ 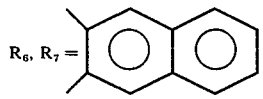

A solution of 1.10 g. of the ketone obtained according to (b) in 80 ml. of absolute dimthoxyethane was mixed with 80 ml. of ethereal zinc borohydride solution (see Example 1[c]) and agitated for 14 hours at room temperature. After adding water, the mixture was extracted with ether, the extract shaken with brine, dried over magnesium sulfate, and evaporated to dryness under vacuum. After chromatography of the residue on silica gel (hexane/ether = 3 + 7), 438 mg. of the above α-alcohol was obtained as a colorless oil, as well as 380 mg. of the corresponding β-alcohol (1S,5R,6R,7R,3'S)-6-[(E)-3-hydroxy-4,4-(naphthylene-2,3-dioxy)-1-butenyl]-7-benzoyloxy-2-oxabicyclo[3,3,0]octan-3-one as a colorless oil.

IR (α-alcohol): 3600, 1775, 1720, 1600, 1470, 970, 855 cm$^{-1}$
TLC (ether): Rf value = 0.26 (α-alcohol)
0.24 (β-alcohol).

d.
(1S,5R,6R,7R,3'R)-6-[(E)-4,4-(Naphthylene-2,3-dioxy)-1-butenyl]-3',7-dihydroxy-2-oxabicyclo 3,3,0]octan-3-one Formula C: $A = \text{trans-CH}=\text{CH}$; $R_4 = OH$; $R_5 = R_8 = H$;

$R_6, R_7 =$ 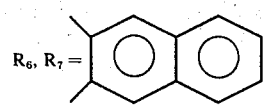

138 mg. of potassium carbonate (anhydrous) was added to a solution of 400 mg. of the α-alcohol obtained according to (c) in 20 ml. of absolute methanol. The mixture was stirred for 2.5 hours at room temperature under argon, then combined with 20 ml. of 0.1N hydrochloric acid, diluted with brine, and extracted with ethyl acetate. The organic phase was washed with brine, dried over magnesium sulfate, and evaporated under vacuum. After chromatography of the residue on silica gel (ether/ethyl acetate = 7 + 3), 211 mg. of the above diol was obtained as colorless crystals, m.p. 162°–164° C.

IR: 3600, 1775, 1600, 1470, 980, 855 cm$^{-1}$ e. (1S,5R,6R,7R,3'R)-6-[(E)-4,4-(Naphthylene-2,3-dioxy)-1-butenyl]-3',7-bis(tetrahydropyranyl-oxy)-2-oxabicyclo[3,3,-0]octan-3-one Formula D: $A = \text{trans-CH}=\text{CH}$; $R_4' = OTHP$;
$R_5' = R_8 = H$; $R_6, R_7 =$ 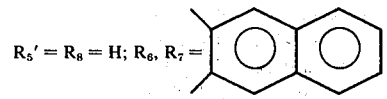

482 mg. of the diol obtained according to (d), 1.30 ml. of freshly distilled dihydropyran, and 10 mg. of p-toluenesulfonic acid in 12 ml. of absolute methylene chloride were agitated for 15 minutes at room temperature. After dilution with methylene chloride, the mixture was extracted with sodium bicarbonate solution and water, dried over magnesium sulfate, and evaporated to dryness under vacuum. After filtering the residue over 6 g. of silica gel (ether/hexane = 7 + 3), 562 mg. of the above bis(tetrahydropyranyl) ether was obtained as colorless crystals, m.p. 58° C.

IR: 1775, 1600, 1470, 1150, 980, 855 cm$^{-1}$
TLC (ether): Rf value = 0.36.

f. (2 RS,3aR,4R,5R,6aS,3'R)-4-[(E)-4,4-Naphthylene-2,3dioxyl)-1-butenyl]-2-hydroxy-;b 3',5-bis(tetrahydropyranyloxy)-perhydrocyclopenta[b]furan Formula E: $A = \text{trans-CH}=\text{CH}$; $R_4' = OTHP$; $R_5' = R_8 = H$;

$R_6, R_7 =$ 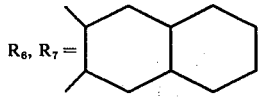

4 ml. of a 20% solution of diisobutylaluminum hydride in toluene was added dropwise to a solution, cooled to −60° C., of 558 mg. of the bis(tetrahydropyranyl) ether produced according to (e) in 15 ml. of absolute toluene; the mixture was then stirred for 30 minutes at −60° C. The reaction was terminated by the dropwise addition of 1 ml. of isopropanol. After the addition of 30 ml. of water, the mixture was stirred for 15 minutes at 0° C., extracted with ethyl acetate, dried over magnesium sulfate, and evaporated to dryness under vacuum, yielding 542 mg. of the above lactol as a colorless oil.

IR: 3600, 1600, 1470, 1150, 980, 855 cm$^{-1}$ g.
(5Z,13E)-(8R,9S,11R,12R,15R)-9-Hydroxy-11,15-bis(tetrahydropyranyloxy)-16,16-(naphthylene-2,3-dioxy)-17,18,19,20-tetranor-prostadienoic Acid Formula II: A = trans-CH=CH; R$_1$ = CO$_2$H; R$_2$ = OH; R$_3$ = R$_5$' = R$_8$ = H; R$_4$' = OTHP;

R$_6$, R$_7$ = 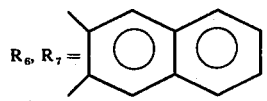

To a solution of 2.50 g. of 4-carboxybutyltriphenylphosphonium bromide in 8 ml. of absolute DMSO was added 9.1 ml. of a solution of methanesulfinylmethylsodium in absolute DMSO (see Example 1[g]). The mixture was stirred for 30 minutes at room temperature. To this solution was added dropwise 660 mg. of the lactol obtained according to (f), dissolved in 8 ml. of absolute DMSO, and the mixture was agitated for 2 hours at 45° C. Then, the mixture was poured on ice water and extracted three times with methylene chloride. The aqueous phase was acidified to pH 4 with aqueous citric acid solution and extracted four times with an ether/hexane mixture 2:1. The ether/hexane extract was shaken with brine, dried over magnesium sulfate, and evaporated under vacuum. The residue was chromatographed on silica gel and eluted with ether, yielding 410 mg. of the above-mentioned prostadienoic acid as a colorless oil.

IR: 3600-3300, 1710, 1600, 1470, 1150, 980, 855 cm$^{-1}$

EXAMPLE 12
(5Z,13E)-(8R,9S,11R,12R,15S)-9,11,15-Trihydroxy-16,16-(naphthylene-2,3-dioxy)-17,18,19,20-tetranor-prostadienoic Acid Formula I: A = trans-CH=CH; B = cis-CH=CH; R$_1$ = CO$_2$H;
X---Y = CH$_2$—CH; R$_2$ = R$_5$ = OH; R$_3$ = R$_4$ = R$_8$ = H;

OH

R$_6$, R$_7$ = 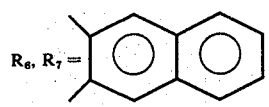

Analogously to Example 11, the above prostadienoic acid was obtained from the corresponding starting substances as a slightly yellowish oil.

IR: 3600–3300, 1710, 1600, 1470, 980, 855 cm$^{-1}$

EXAMPLE 13
(5Z,13E)-(8R,11R,12R,15R)-11,15-Dihydroxy-9-oxo-16,16-(naphthylene-2,3-dioxy)-17,18,19,20-tetranor-prostadienoic Acid Formula I: A = trans-CH=CH; B = cis-CH=CH;
X---Y = CH$_2$—CH; R$_1$ = CO$_2$H; R$_2$, R$_3$ = O;

OH

R$_4$ = OH; R$_5$ = R$_8$ = H; R$_6$, R$_7$ = 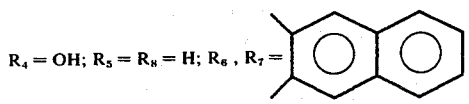

232 mg. of (5Z,13E)-(8R,11R,12R,15R)-11,15-bis(tetrahydropyranyloxy)-9-oxo-16,16-(naphthylene-2,3-dioxy)-17,18,19,20-tetranor-prostadienoic acid was agitated for 5 hours in 5 ml. of a mixture of acetic acid/water/tetrahydrofuran (65/35/10) and then evaporated to dryness under vacuum. The residue was chromatographed on silica gel (chloroform/ethanol = 95 + 5), thus obtaining 113 mg. of the aforementioned compound as a colorless oil.

IR: 3600–3300, 1740, 1705, 1470, 980, 855 cm$^{-1}$

The starting material for the above compound was prepared as follows:

(5Z,13E)-(8R,11R,12R,15R)-11,15-Bis(tetrahydropyranyloxy)-9-oxo-16,16-(naphthylene-2,3-dioxy)-17,18,19,20-tetranorprostadienoic Acid Formula II: A = trans-CH=CH; R$_1$ = CO$_2$H; R$_2$, R$_3$ = O;

R$_4$' = OTHP; R$_5$' = R$_8$ = H; R$_6$, R$_7$ = 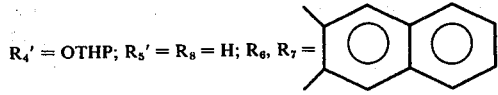

347 mg. of the substance obtained according to Example 11(g) was dissolved in 8 ml. of acetone and combined at −20° C. with 0.14 ml. of Jones reagent (see Example 7[a]). After 15 minutes, the excess reagent was destroyed by adding 0.5 ml. of isopropanol. The mixture was then diluted with 40 ml. of water and three times extracted with methylene chloride. The organic extract was shaken with brine, dried over magnesium sulfate, and concentrated under vacuum, thus producing 262 mg. of the above compound as an oil having a slightly yellow color.

IR: 3600–3300, 1740, 1705, 1600, 1470, 980, 855 cm$^{-1}$

EXAMPLE 14

According to Example 13, the following prostaglandin E analog can be prepared:

(5Z,13E)-(8R,11R,12R,15S)-11,15-dihydroxy-9-oxo-16,16-(naphthylene-2,3-dioxy)-17,18,19,20-tetranor-prostadienoic acid, colorless oil.

IR: 3600–3400, 1740, 1705, 1600, 1470, 980, 855 cm$^{-1}$

EXAMPLE 15 (5Z,13E)-(8R,9S,11R,12R,15R)-9,11,15-Trihydroxy-15-(5,5-dimethyl-1,3-dioxan-2-yl)-16,17,18,19,20-pentanor-prostadienoic Acid Formula I:  A = trans-CH=CH; B = cis-CH=CH; X---Y = CH$_2$—CH;
                                                              |
                                                              OH $R_1 = CO_2H$; $R_2 = R_4 = OH$;
$R_3 = R_5 = R_8 = H$; $R_6, R_7 = CH_2-C(CH_3)_2-CH_2$ 140 mg. of (5Z,13E)-(8R,9S,11R,12R,15R)-9-hydroxy-11,15-bis(tetrahydropyranyloxy)-15-(5,5-dimethyl-1,3-dioxan-2-yl)-16,17,18,19,20-pentanor-prostadienoic acid was agitated in 4 ml. of a mixture of acetic acid/water/tetrahydrofuran = 65/35/10 for 4 hours at 40° C. and then evaporated under vacuum. After column chromatography on 5 g. of silica gel (chloroform/ethanol = 4 + 1), 53 mg. of the above compound was produced as a colorless oil.

IR: 3600–3300, 1710, 1150, 980 cm$^{-1}$

The starting materials were prepared as follows:

a. Analogously to Example 1(a), 3,3-[(2,2-dimethyl)-trimethylene-1,3-dioxy]-acetonylidenetriphenylphosphorane was produced; colorless crystals were obtained, m.p. 140° C.

The methyl ester of 5,5-dimethyl-1,3-dioxane-2-carboxylic acid required for preparing the above compound was formed as follows:

A solution of 15.6 g. of 2,2-dimethylpropane-1,3-diol in 30 ml. of absolute dimethylformamide was added dropwise to a suspension of 14.4 g. of sodium hydride (50% strength in oil) in 120 ml. of absolute dimethylformamide; the mixture was agitated for 12 hours at room temperature and then a solution of 12.8 g. of dichloroacetic acid in 30 ml. of dimethoxyethane was added dropwise thereto. The mixture was stirred for another 14 hours at room temperature and then evaporated to dryness under vacuum. The remaining solid salt was dissolved in water and extracted three times with ether. The aqueous phase was gently adjusted to pH 3 at 0° C. with 10% sulfuric acid and extracted four times with ether. The combined ether extracts were shaken twice with brine, dried over magnesium sulfate, and evaporated under vacuum. The thus-obtained acid was converted without purification into the methyl ester in methylene chloride solution by the addition of ethereal diazomethane solution. After the ester had been distilled under vacuum, 6.80 g. was obtained as colorless crystals; b.p.$_{14}$ = 105° C.

b. Analogously to Example 1(b), using the phosphorane prepared according to (a), one obtains (1S,5R,6R,7R)-6-[(E)-3-oxo-3-(5,5-dimethyl-1,3-dioxan-2-yl)-1-propenyl]-7-benzoyloxy-2-oxabicyclo[3,3,0]octan-3-one, m.p. 141° C.

IR: 1775, 1720, 1690, 1640, 1600, 1150, 980 cm$^{-1}$ c. In analogy to Example 1(c), using 2.80 g. of the ketone obtained according to (b), the thus-formed products are 1.30 g. of (1S,5R,6R,7R,3'R)-6-[(E)-3-hydroxy-3-(5,5-dimethyl-1,3-dioxan-2-yl)-1-propenyl]-7-benzoyloxy-2-oxabicyclo[3,3,0]-octan-3-one (α-alcohol) and 1.10 g. of (1S,5R,6R,7R,3'S)-6-[(E)-3-hydroxy-3-(5,5-dimethyl-1,3-dioxan-2-yl)-1-propenyl]-7-benzoyloxy-2-oxabicyclo[3,3,0]octan-3-one (β-alcohol), both products being colorless oils.

IR:

(α-alcohol): 3600, 1775, 1715, 1600, 1120, 980 cm$^{-1}$ (β-alcohol): 3600, 1775, 1715, 1600, 1125, 980 cm$^{-1}$ d.
(1S,5R,6R,7R,3'R)-6-[(E)-3-(5,5-Dimethyl-1,3-dioxan-2-yl)-1-propenyl]-3',7-dihydroxy-2-oxabicyclo[3,3,0]octan-3-one Formula C: A = trans-CH=CH; $R_4$ = OH; $R_5 = R_8$ = H; $R_6, R_7 = CH_2-C(CH_3)_2-CH_2$ Analogously to Example 1(d), 1.40 g. of the β-alcohol produced according to (c) yielded 1.02 g. of the above compound as a colorless oil.

IR: 3600, 1775, 1150, 980 cm$^{-1}$ e.
(1S,5R,6R,7R,3'R)-6-[(E)-3-(5,5-Dimethyl-1,3-dioxan-2-yl)-1-propenyl]-3',7-bis(tetrahydropyranyloxy)-2-oxabicyclo[3,3,0]octan-3-one Formula D: A = trans-CH=CH; $R_4'$ = OTHP; $R_5'$ = $R_8$ = H; $R_6, R_7 = CH_2-C(CH_3)_2-CH_2$ Analogously to Example 1(e), 970 mg. of the diol obtained according to (d) yielded 1.08 g. of the above compound as a colorless oil.

IR: 1775, 1150, 980 cm$^{-1}$ f. (2RS, 3aR,4R,5R,6aS,3'R)-4-[(E)-3-(5,5-Dimethyl-1,3-dioxan-2-yl)-1-propenyl]-2-hydroxy-3',5-bis(tetrahydropyranyloxy)-perhydrocyclopenta-[b]furan Formula E: A = trans-CH=CH; $R_4'$ = OTHP; $R_5'$ = $R_8$ = H; $R_6, R_7 = CH_2-C(CH_3)_2-CH_2$ Analogously to Example 1(f), the above substance was obtained from the compound produced according to (e) as a colorless oil.

IR: 3600, 1150, 980 cm$^{-1}$ (g) (5Z,13E)-(8R,9S,11R,12R,15R)-9-Hydroxy-11,15-bis(tetrahydropyranyloxy)-15-(5,5-dimethyl-1,3-dioxan-2-yl)-16,17,18,19,20-pentanorprostadienoic Acid Formula II: A = trans-CH=CH; $R_1$ = $CO_2H$; $R_2$ = $_{OH}$;
$R_3$ = $R_5'$ = $R_8$ = H; $R_4'$ = OTHP; $R_6,R_7$ = $CH_2$-
$C(CH_3)_2$-$CH_2$ In analogy to Example 1(g), 390 mg. of a lactol produced according to (f) yielded 275 mg. of the above compound as a colorless oil.

IR: 3600–3300, 1710, 1120, 980 cm$^{-1}$

EXAMPLE 16

(5Z,13E)-(8R,R,R,12R,15R)-11,15-Dihydroxy-9-oxo-15-(5,5-dimethyl-1,3-dioxan-2-yl)-16,17,18,19,20-pentanorprostadienoic Acid Formula I:  A = trans-CH=CH; B = cis-CH=CH; X$\cdots$Y = $CH_2$—CH;
OH $R_1$ = $CO_2H$; $R_2$, $R_3$ = O; $R_4$ = OH;
$R_5$ = $R_8$ = H; $R_6$, $R_7$ = $CH_2$—$C(CH_3)_2$—$CH_2$ In analogy to Example 7, 334 mg. of (5Z,13E)-(8R,11R,12R,15R)-11,15-bis(tetrahydropyranyloxy)-9-oxo-15-(5,5-dimethyl-1,3-dioxan-2-yl)-16,17,18,19,20-pentanorprostadienoic acid yielded 95 mg. of the above compound as a colorless oil.

IR: 3600–3300, 1740, 1705, 1150, 980 cm$^{-1}$

The starting material was produced as follows:

a. (5Z,13E)-(8R,11R,12R,15R)-11,15-Bis(tetrahydropyranyloxy)-9-oxo-15-(5,5-dimethyl-1,3-dioxan-2-yl)-16,17,18,19,20-pentanor-prostadienoic Acid Formula II: A = trans-CH=CH; $R_1$ = $CO_2H$; $R_2,R_3$ = O; $R_4'$ = OTHP; $R_5'$ = $R_8$ = H; $R_6,R_7$ = $CH_2$-$C(CH_3)_2$-$CH_2$ By Jones oxidation of 413 mg. of the compound prepared according to Example 15(g), 305 mg. of the above compound was obtained as a colorless oil, by proceeding in accordance with Example 7(a).

IR: 3600–3300, 1740, 1710, 1150, 980 cm$^{-1}$

EXAMPLE 17

According to the processes described in Examples 1, 2, 7, and 8, with the use of the appropriate starting compounds, the following prostaglandin analogs can be prepared:

(5Z,13E)-(8R,9S,11R,12R,15R)-9,11,15-trihydroxy-16,16-(naphthylene-2,3-dioxy)-17,18,19,20-tetranor-prostadienoic acid; (5Z,13E)-(8R,9S,11R,12R,15S)-9,11,15-trihydroxy-16,16-(naphthylene-2,3-dioxy)-17,18,19,20-tetranor-prostadienoic acid; (5Z)-(8R,9S,11R,12R,15R)-9,11,15-trihydroxy-16,16-(naphthylene-2,3-dioxy)-17,18,19,20-tetranor-prostenoic acid; (5Z)-(8R,9S,11R,12R,15S)-9,11,15-trihydroxy-16,16-naphthylene-2,3-dioxy)-17,18,19,20-tetranor-prostenoic acid; (5Z,13E)-(8R,11R,12R,15R)-11,15-dihydroxy-9-oxo-16,16-(naphthylene-2,3-dioxy)-17,18,19,20-tetranor-prostadienoic acid; (5Z,13E)-(8R,11R,12R,15S)-11,15-dihydroxy-9-oxo-16,16-(naphthylene-2,3-dioxy)-17,18,19,20-tetranor-prostadienoic acid; (5Z)-(8R,11R,12R,15R)-11,15-dihydroxy-9-oxo-16,16-(naphthylene-2,3-dioxy)-17,18,19,20-tetranor-prostenoic acid; (5Z)-(8R,11R,12R,15S)-11,15-dihydroxy-9-oxo-16,16-(naphthylene-2,3-dioxy)-17,18,19,20-tetranor-prostenoic acid.

EXAMPLE 18

(5Z,10Z,13E)-(8R,12S,15R)-15-Hydroxy-9-oxo-15-(1,3-dioxa-2-indanyl)-16,17,18,19,20-pentanor-prostatrienoic Acid Formula I: A = trans-CH=CH; B = cis-CH=CH;
X=Y = CH=CH; $R_1$ = $CO_2H$; $R_2,R_3$ = O; $R_4$ = OH; $R_5$ = $R_8$ = H; $R_6,R_7$ = 1,2-phenylene A solution of 85 mg. of (5Z,13E)-(8R,11R,12R,15R)-11,15-dihydroxy-9-oxo-15-(1,3-dioxa-2-indanyl)-16,17,18,19,20-pentanor-prostadienoic acid (from Example 7) in 6 ml. of 90% acetic acid was agitated for 19 hours at 60° C. and then evaporated under vacuum. Chromatography on 7 g. of silica gel (ether/3% dioxane) yielded 42 mg. of the title compound as a slightly yellow oil.

IR: 3600–3300, 1715, 1700, 1585, 1500, 980 cm$^{-1}$

EXAMPLE 19

According to the process described in Example 18, the following prostaglandin A analogs can be produced with the use of the corresponding starting materials:

(5Z,10Z,13E)-(8R,12S,15R)-15-hydroxy-9-oxo-15-(5,5-dimethyl-1,3-dioxan-2-yl)-16,17,18,19,20-pentanor-prostartrienoic acid; (5Z,10Z,13E)-(8R,12S,15R)-15-hydroxy-9-oxo-16,16-(naphthylene-2,3-dioxy)-17,18,19,20-tetranor-prostatrienoic acid; (5Z,10Z,13E)-(8R,12S,15S)-15-hydroxy-9-oxo-16,16-(naphthylene-2,3-dioxy)-17,18,19,20-tetranor-prostatrienoic acid.

EXAMPLE 20

(13E)-(8R,9S,11R,12R,15R)-9,11,15-Trihydroxy-15-(1,3-dioxa-2-indanyl)-16,17,18,19,20-pentanor-prostenoic Acid Formula I:  A = trans-CH=CH; B = $CH_2$—$CH_2$; X$\cdots$Y = $CH_2$—CH;
OH $R_1$ = $CO_2H$; $R_2$ = $R_4$ = OH; $R_3$ = $R_5$ = $R_8$ = H;
$R_6$, $R_7$ = 1,2-phenylene A mixture of 150 mg. of (5Z,13E)-(8R,9S,11R,12R,15R)-9,11,15-trihydroxy-15-(1,3-dioxa-2-indanyl)-16,17,18,19,20-pentanor-prostadienoic acid, 15 mg. of 10% palladium on charcoal, and 15 ml. of ethyl acetate was agitated for 2 hours at −20° C. under a hydrogen atmosphere. After filtration through a glass suction filter, the mixture was evaporated to dryness under vacuum, thus obtaining 145 mg. of the title compound as a colorless oil.

IR: 3600–3300, 1710, 980 (trans-double bond) cm$^{-1}$

The NMR spectrum in CDCl$_3$ shows only two olefinic protons.

EXAMPLE 21

By proceeding according to the process described in Example 20, the following prostaglandin analogs of the one-series are obtained with the use of the corresponding starting compounds:

(13E)-(8R,11R,12R,15R)-11,15-dihydroxy-9-oxo-15-(1,3-dioxa-2-indanyl)-16, 17, 18, 19, 20-pentanor-prostenoic acid; (13E)-(8R,11R,12R,15R)-11,15-dihydroxy-9-oxo-16,16-(naphthylene-2,3-dioxy)-17, 18, 19, 20-tetranor-prostenoic acid; (13E)-(8R,9S,11R,12R,15R)-9, 11, 15-trihydroxy-16,16-(naphthylene-2,3-dioxy)-17, 18, 19, 20-tetranor-prostenoic acid; (13E)-(8R,9S,11R,12R,15R)-9, 11, 15-trihydroxy-15-(5,5-dimethyl-1,3-dioxan-2-yl)-16, 17, 18, 19, 20-pentanor-prostenoic acid; (13E)-(8R,11R,12R,15R)-11,15-dihydroxy-9-oxo-15-(5,5-dimethyl-1,3-dioxan-2-yl)-16, 17, 18, 19, 20-pentanor-prostenoic acid.

EXAMPLE 22

(8R,9S,11R,12R,15R)-9,11,15-Trihydroxy-15-(1,3-dioxa-2-indanyl)-16,17,18,19,20-pentanor-prostanoic Acid Formula I: $A = B = CH_2—CH_2$; $X \text{---} Y = CH_2—CH$;

$R_1 = CO_2H$; $R_2 = R_4 = OH$; $R_3 = R_5 = R_8 = H$;
$R_6, R_7 = $ 1,2-phenylene A mixture of 404 mg. of the prostadienoic acid prepared according to Example 1, 40 mg. of palladium on charcoal (10%), and 10 ml. of ethyl acetate was shaken until 2 millimoles of hydrogen had been absorbed under a hydrogen atmosphere at room temperature. After filtration and evaporation, 400 mg. of the above prostanoic acid was obtained as a colorless oil.

IR: 3600–3300, 1710, 1500 cm$^{-1}$

EXAMPLE 23

(5Z,13E)-(8R,9S,11R,12R,15R)-9,11,15-Trihydroxy-15-(1,3-dioxa-2-indanyl)-16,17,18,19,20-pentanor-prostadienoic Acid Methyl Ester Formula I: $A = $ trans-$CH=CH$; $B = $ cis-$CH=CH$;

$X \text{---} Y = CH_2—CH$; $R_1 = CO_2CH_3$; $R_2 = R_4 = OH$;

OH

-continued $R_3 = R_5 = R_8 = H$; $R_6, R_7 = $ 1,2-phenylene

An ethereal diazomethane solution was added dropwise to a solution of 100 mg. of the prostadienoic acid obtained according to Example 1 in 5 ml. of methylene chloride, until the yellow color became permanent. After 2 minutes, the mixture was evaporated under vacuum at room temperature, thus obtaining 104 mg. of the title compound as colorless crystals, m.p. 74°–75° C. (from isopropyl ether/methylene chloride).

IR: 3600, 1735, 1500, 980 cm$^{-1}$

TLC (ether/dioxane = 8 + 2): Rf value = 0.33.

Analogously to Example 23, all other prostaglandin acids described in the above examples can also be converted into the methyl esters thereof.

Replacing the diazomethane employed in Example 23 by diazoethane, diazobutane, and diazodecane leads to the corresponding ethyl, butyl, and decyl esters, respectively.

EXAMPLE 24

(5Z,13E)-(8R,9S,11R,12R,15R)-9,11,15-Trihydroxy-15-(1,3-dioxa-2-indanyl)-16,17,18,19,20-pentanor-prostadienoic Acid p-Phenylphenacyl Ester Formula I: $A = $ trans-$CH=CH$; $B = $ cis-$CH=CH$;

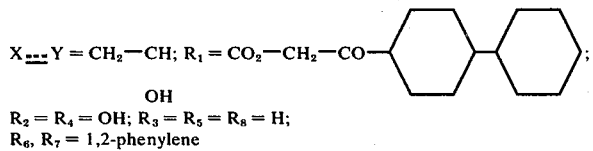

$X \text{---} Y = CH_2—CH$; $R_1 = CO_2—CH_2—CO—$

OH
$R_2 = R_4 = OH$; $R_3 = R_5 = R_8 = H$;
$R_6, R_7 = $ 1,2-phenylene 70 mg. of the prostadienoic acid obtained according to Example 1 was agitated with 21 mg. of triethylamine and 53 mg. of p-phenylphenacyl bromide in 4 ml. of acetone for 12 hours at room temperature under argon. After dilution with water, the mixture was extracted with ether, the ether extract was shaken with NaCl solution, dried over magnesium sulfate, and evaporated under vacuum. The residue was filtered over 5 g. of silica gel with ether/dioxane mixtures. After recrystallization from methylene chloride/hexane, 51 mg. of the title compound was obtained in the form of colorless crystals, m.p. 121° C.

IR: 3600, 1740, 1695, 1500, 980 cm$^{-1}$

TLC (ether/dioxane = 8 + 2): Rf value = 0.45.

Analogously to Example 24, all other prostaglandin acids described in the above examples can also be converted into the corresponding phenacyl esters.

EXAMPLE 25

Tris(hydroxymethyl)aminomethane Salt of (5Z,13E)-(8R,9S,11R,-12R,15R)-9,11,15-Trihydroxy-15-(1,3-dioxa-2-indanyl)-16,17,18,19,20-pentanor-prostadienoic Acid At 60° C., a solution of 32.9 mg. of tris(hydroxymethyl)aminomethane in 0.1 ml. of water was added to a solution of 100 mg. of the prostadienoic acid produced according to Example 1 in 14 ml. of acetonitrile; the mixture was allowed to stand for 14 hours at room temperature. Yield: 76 mg. of the above salt as colorless crystals.

Analogously to Example 25, all other prostaglandin acids described in the above examples can also be converted into the corresponding tris(hydroxymethyl)aminomethane salts.

EXAMPLE 26

Analogously to Examples 23 and 24, the methyl, ethyl, butyl, and p-phenylphenacyl esters of the following acids are prepared:

(5Z,13E)-(8R,9S,11R,12R,15R)-9,11,15-trihydroxy-15-(1,3-dioxa-2-indanyl)-16,17,18,19,20-pentanor-prostadienoic acid;

(5Z,13E)-(8R,9S,11R,12R,15S)-9,11,15-trihydroxy-15-(1,3-dioxa-2-indanyl)-16,17,18,19,20-pentanor-prostadienoic acid;

(5Z)-(8R,9S,11R, 12R,15R)-9,11,15-trihydroxy-15-(1,3-dioxa-2-indanyl)-16,17,18,19,20-pentanor-prostenoic acid;

(5Z)-(8R,9S,11R,12R,15S)-9,11,15-trihydroxy-15-(1,3-dioxa-2-indanyl)-16,17,18,19,20-pentanor-prostenoic acid;

(5Z,13E)-(8R,11R,12R,15R)-11,15-dihydroxy-9-oxo-15-(1,3-dioxa-2-indanyl)-16,17,18,19,20-pentanor-prostadienoic acid;

(5Z,13E)-(8R,11R,12R,15S)-11,15-dihydroxy-9-oxo-15-(1,3-dioxa-2-indanyl)-16,17,18,19,20-pentanor-prostadienoic acid;

(5Z)-(8R,11R,12R,15R)-11,15-dihydroxy-9-oxo-15-(1,3-dioxa-2-indanyl)-16,17,18,19,20-pentanor-prostenoic acid;

(5Z)-(8R,11R,12R,15S)-11,15-dihydroxy-9-oxo-15-(1,3-dioxa-2-indanyl)-16,17,18,19,20-pentanor-prostenoic acid;

(5Z,13E)-(8R,9S,11R,12R,15R)-9,11,15-trihydroxy-15-(5,5-dimethyl-1,3-dioxan-2-yl)-16,17,18,19,20-pentanor-prostadienoic acid;

(5Z,13E)-(8R,11R,12R,15R)-11,15-dihydroxy-9-oxo-15-(5,5-dimethyl-1,3-dioxan-2-yl)-16,17,18,19,20-pentanor-prostadienoic acid;

(5Z,10Z,13E)-(8R,12S,15R)-15-hydroxy-9-oxo-15-(1,3-dioxa-2-indanyl)-16,17,18,19,20-pentanor-prostatrienoic acid;

(5Z,10Z,13E)-(8R,12S,15R)-15-hydroxy-9-oxo-15-(5,5-dimethyl-1,3-dioxan-2-yl)-16,17,18,19,20-pentanor-prostatrienoic acid;

(13E)-(8R,9S,11R,12R,15R)-9,11,15-trihydroxy-15-(1,3-dioxa-2-indanyl)-16,17,18,19,20-pentanor-prostenoic acid;

(13E)-(8R,11R,12R,15R)-11,15-dihydroxy-9-oxo-15-(1,3-dioxa-2-indanyl)-16,17,18,19,20-pentanor-prostenoic acid;

(13E)-(8R,9S,11R,12R,15R)-9,11,15-trihydroxy-15-(5,5-dimethyl-1,3-dioxan-2-yl)-16,17,18,19,20-pentanor-prostenoic acid;

(13E)-(8R,11R,12R,15R)-11,15-dihydroxy-9-oxo-15-(5,5-dimethyl-1,3-dioxan-2-yl)-16,17,18,19,20-pentanor-prostenoic acid;

(8R,9S,11R,12R,15R)-9,11,15-trihydroxy-15-(1,3-dioxa-2-indanyl)-16,17,18,19,20-pentanor-prostanoic acid;

(5Z,13E)-(8R,9S,11R,12R,15R)-9,11,15-trihydroxy-16,16-(naphthylene-2,3-dioxy)-17,18,19,20-tetranor-prostadienoic acid;

(5Z,13E)-(8R,9S,11R,12R,15S)-9,11,15-trihydroxy-16,16-(naphthylene-2,3-dioxy)-17,18,19,20-tetranor-prostadienoic acid;

(5Z)-(8R,9S,11R,12R,15R)-9,11,15-trihydroxy-16,16-(naphthylene-2,3-dioxy)-17,18,19,20-tetranor-prostenoic acid;

(5Z)-(8R,9S,11R,12R,15S)-9,11,15-trihydroxy-16,16-(naphthylene-2,3-dioxy)-17,18,19,20-tetranor-prostenoic acid;

(5Z,13E)-(8R,11R,12R,15R)-11,15-dihydroxy-9-oxo-16,16-(naphthylene-2,3-dioxy)-17,18,19,20-tetranor-prostadienoic acid;

(5Z,13E)-(8R,11R,12R,15S)-11,15-dihydroxy-9-oxo-16,16-(naphthylene-2,3-dioxy)-17,18,19,20-tetranor-prostadienoic acid;

(5Z)-(8R,11R,12R,15R)-11,15-dihydroxy-9-oxo-16,16-(naphthylene-2,3-dioxy)-17,18,19,20-tetranor-prostenoic acid;

(5Z)-(8R,11R,12R,15S)-11,15-dihydroxy-9-oxo-16,16-(naphthylene-2,3-dioxy)-17,18,19,20-tetranor-prostenoic acid;

(5Z,10Z,13E)-(8R,12S,15R)-15-hydroxy-9-oxo-16,16-(naphthylene-2,3-dioxy)-17,18,19,20-tetranor-prostatrienoic acid;

(5Z,10Z,13E)-(8R,12S,15S)-15-hydroxy-9-oxo-16,16-(naphthylene-2,3-dioxy)-17,18,19,20-tetranor-prostatrienoic acid.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A prostaglandin of the formula

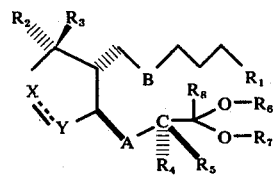

wherein $R_1$ is hydroxymethyl, carboxy, aryloxycarbonyl, alkoxycarbonyl of 1–8 carbon atoms in the alkoxy group, or the group -COO-CH$_2$-U-V wherein U is a direct C—C bond, carbonyl or carbonyloxy and V is phenyl substituted by phenyl, alkoxy of 1-2 carbon atoms or halogen; $R_2$ is hydroxy and $R_3$ is a hydrogen atom or $R_2$ and $R_3$ collectively are an oxygen atom; A is trans-CH=CH; B is -CH$_2$-CH$_2$ or cis-CH=CH; one of $R_4$ and $R_5$ is hydroxy and the other is a hydrogen atom; $R_6$ and $R_7$ collectively are alkylene of up to 7 carbon atoms and with 2-3 carbon atoms in the chain, phenylene or naphthylene; $R_8$ is a hydrogen atom or alkyl of 1-5 carbon atoms,

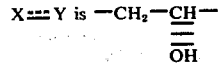

when $R_2$ is hydroxy and $R_3$ is a hydrogen atom or is

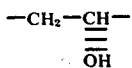

or -CH=CH- when $R_2$ and $R_3$ collectively are an oxygen atom; or, when $R_1$ is carboxy, a physiologically acceptable salt thereof.

2. A compound of claim 1 wherein $R_8$ is a hydrogen atom.

3. A compound of claim 2 wherein $R_1$ is carboxy or a physiologically acceptable salt thereof with a base.

4. A compound of claim 2 wherein $R_1$ is alkoxycarbonyl of 1–8 carbon atoms in the chain.

5. A compound of claim 2 wherein $R_1$ is -COO-$CH_2$-U-V wherein U is a direct C—C bond, carbonyl or carbonyloxy and V is phenyl substituted by phenyl, alkoxy of 1–2 carbon atoms or halogen.

6. A compound of claim 1, (5Z,13E)-(8R,9S,11R,12R,15R)-9,11,15-trihydroxy-15-(1,3-dioxa-2-indanyl)-16,17,18,19,20-pentanor-prostadienoic acid.

7. A compound of claim 1, (5Z,13E)-(8R,9S,11R,12R,15S)-9,11,15-trihydroxy-15-(1,3-dioxa-2-indanyl)-16,17,18,19,20-pentanor-prostadienoic acid.

8. A compound of claim 1, (5Z,13E)-(8R,11R,12R,15R)-11,15-dihydroxy-9-oxo-15-(1,3-dioxa-2-indanyl)-16,17,18,19,20-pentanor-prostadienoic acid.

9. A compound of claim 1, (5Z,13E)-(8R,11R,12R,15S)-11,15-dihydroxy-9-oxo-15-(1,3-dioxa-2-indanyl)-16,17,18,19,20-pentanor-prostadienoic acid.

10. A compound of claim 1, (5Z,13E)-(8R,9S,11R,12R,15R)-9,11,15-trihydroxy-15-(5,5-dimethyl-1,3-dioxan-2-yl)-16,17,18,19,20-pentanor-prostadienoic acid.

11. A compound of claim 1, (5Z,13E)-(8R,11R,12R,15R)-11,15-dihydroxy-9-oxo-15-(5,5-dimethyl-1,3-dioxan-2-yl)-16,17,18,19,20-pentanor-prostadienoic acid.

12. A compound of claim 1, (13E)-(8R,9S,11R,12R,15R)-9,11,15-trihydroxy-15-(1,3-dioxa-2-indanyl)-16,17,18,19,20-pentanor-prostenoic acid.

13. A compound of claim 1, (13E)-(8R,11R,12R,15R)-11,15-dihydroxy-9-oxo-15-(1,3-dioxa-2-indanyl)-16,17,18,19,20-pentanor-prostenoic acid.

14. A compound of claim 1, (13E)-(8R,9S,11R,12R,15R)-9,11,15-trihydroxy-15-(5,5-dimethyl-1,3-dioxan-2-yl)-16,17,18,19,20-pentanor-prostenoic acid.

15. A compound of claim 1, (13E)-(8R,11R,12R,15R)-11,15-dihydroxy-9-oxo-15-(5,5-dimethyl-1,3-dioxan-2-yl)-16,17,18,19,20-pentanor-prostenoic acid.

16. A compound of claim 1, (5Z,13E)-(8R,9S,11R,12R,15R)-9,11,15-trihydroxy-15-(1,3-dioxa-2-indanyl)-16,17,18,19,20-pentanor-prostadienoic acid methyl ester.

17. A compound of claim 1, (5Z,13E)-(8R,9S,11R,12R,15R)-9,11,15-trihydroxy-15-(1,3-dioxa-2-indanyl)-16,17,18,19,20-pentanor-prostadienoic acid p-phenylphenacyl ester.

18. A compound of claim 1, (5Z,13E)-(8R,9S,11R,12R,15R)-9,11,15-trihydroxy-16,16-(naphthylene-2,3-dioxy)-17,18,19,20-tetranor-prostadienoic acid.

19. A compound of claim 1, (5Z,13E)-(8R,9S,11R,12R,15S)-9,11,15-trihydroxy-16,16-(naphthylene-2,3-dioxy)-17,18,19,20-tetranor-prostadienoic acid.

20. A compound of claim 1, (5Z,13E)-(8R,11R,12R,15R)-11,15-dihydroxy-9-oxo-16,16-(naphthylene-2,3-dioxy)-17,18,19,20-tetranor-prostadienoic acid.

21. A compound of claim 1, (5Z,13E)-(8R,11R,12R,15S)-11,15-dihydroxy-9-oxo-16,16-(naphthylene-2,3-dioxy)-17,18,19,20-tetranor-prostadienoic acid.

22. A compound of claim 1, (5Z,10Z,13E)-(8R,12S,15R)-15-hydroxy-9-oxo-16,16-(naphthylene-2,3-dioxy)-17,18,19,20-tetranor-prostatrienoic acid.

23. A compound of claim 1, (5Z,10Z,13E)-(8R,12R,15S)-15-hydroxy-9-oxo-16,16-(naphthylene-2,3-dioxy)-17,18,19,20-tetranor-prostatrienoic acid.

24. A compound of claim 1, the tris(hydroxymethyl)aminomethane salt of (5Z,13E)-(8R,9S,11R,12R,15R)-9,11,15-trihydroxy-15-(1,3-dioxa-2-indanyl)-16,17,18,19,20-pentanor-prostadienoic acid.

25. A compound of claim 1, the tris(hydroxymethyl)aminomethane salt of (5Z,13E)-(8R,9S,11R,12R,15R)-9,11,15-trihydroxy-16,16-(naphthylene-2,3-dioxy)-17,18,19,20-tetranor-prostadienoic acid.

26. A compound of claim 1, the tris(hydroxymethyl)aminomethane salt of (5Z,13E)-(8R,9S,11R,12R,15S)-9,11,15-trihydroxy-16,16-(naphthylene-2,3-dioxy)-17,18,19,20-tetranor-prostadienoic acid.

27. A compound of claim 1, the methyl, ethyl, butyl, and p-phenylphenacyl esters of an acid of the group consisting of (5Z,13E)-(8R,9S,11R,12R,15R)-9,11,15-trihydroxy-15-(1,3-dioxa-2-indanyl)-16,17,18,19,20-pentanor-prostadienoic acid, (5Z,13E)-(8R,9S,11R,12R,15S)-9,11,15-trihydroxy-15-(1,3-dioxa-2-indanyl)-16,17,18,19,20-petanor-prostadienoic acid, (5Z,13E)-(8R,11R,12R,15R)-11,15-dihydroxy-9-oxo-15-(1,3-dioxa-2-indanyl)-16,17,18,19,20-pentanor-prostadienoic acid, (5Z,13E)-(8R,11R,12R,15S)-11,15-dihydroxy-9-oxo-15-(1,3-dioxa-2-indanyl)-16,17,18,19,20-pentanor-prostadienoic acid, (5Z,13E)-(8R,9S,11R,12R,15R)-9,11,15-trihydroxy-15-(5,5-dimethyl-1,3-dioxan-2-yl)-16,17,18,19,20-pentanor-prostadienoic acid, (5Z,13E)-(8R,11R,12R,15R)-11,15-dihydroxy-9-oxo-15-(5,5-dimethyl-1,3-dioxan-2-yl)-16,17,18,19,20-pentanor-prostadienoic acid, (5Z,10Z,13E)-(8R,12S,15R)-15-hydroxy-9-oxo-15-(1,3-dioxa-2-indanyl)-16,17,18,19,20-pentanor-prostatrienoic acid, (5Z,10Z,13E)-(8R,12S,15R)-15-hydroxy-9-oxo-15-(5,5-dimethyl-1,3-dioxan-2-yl)-16,17,18,19,20-pentanor-prostatrienoic acid, (13E)-(8R,9S,11R,12R,15R)-9,11,15-trihydroxy-15-(1,3-dioxa-2-indanyl)-16,17,18,19,20-pentanor-prostenoic acid, (13E)-(8R,11R,12R,15R)-11,15-dihydroxy-9-oxo-15-(1,3-dioxa-2-indanyl)-16,17,18,19,20-pentanor-prostenoic acid.

(13E)-(8R,9S,11R,15R)-9,11,15-trihydroxy-15-(5,5-dimethyl-1,3-dioxan-2-yl)-16,17,18,19,20-pentanor-prostenoic acid, (13E)-(8R,11R,12R,15R)-11,15-dihydroxy-9-oxo-15-(5,5-dimethyl-1,3-dioxan-2-yl)-16,17,18,19,20-pentanor-prostenoic acid, (5Z,13E)-(8R,9S,11R,12R,15R)-9,11,15-trihydroxy-16,16-(naphthylene-2,3-dioxy)-17,18,19,20-tetranor-prostadienoic acid, (5Z,13E)-(8R,9S,11R,12R,15S)-9,11,15-trihydroxy-16,16-(naphthylene-2,3-dioxy)-17,18,19,20-tetranor-prostadienoic acid, (5Z,13E)-(8R,11R,12R,15R)-11,15-dihydroxy-9-oxo-16,16-(naphthylene-2,3-dioxy)-17,18,19,20-tetranor-prostadienoic acid, (5Z,13E)-(8R,11R,12R,15S)-11,15-dihydroxy-9-oxo-16,16-(naphthylene-2,3-dioxy)-17,18,19,20-tetranor-prostadienoic acid, (5Z,10Z,13E)-(8R,12S,15R)-15-hydroxy-9-oxo-16,16-(naphthylene-2,3-dioxy)-17,18,19,20-tetranor-prostatrienoic acid, and (5Z,10Z,13E)-(8R,12R,15S)-15-hydroxy-9-oxo-16,16-(naphthylene-2,3-dioxy)-17,18,19,20-tetranor-prostatrienoic acid.

28. A pharmaceutical composition comprising a luteolytically effective amount of a compound of claim 1 of the E-, D- or F-type, in admixture with a pharmaceutically acceptable carrier.

29. A sterile aqueous or oily solution containing 0.01 – 100 μg/ml of a compound of claim 20.

* * * * *